United States Patent
Garcia-Bengochea et al.

(10) Patent No.: US 8,025,684 B2
(45) Date of Patent: Sep. 27, 2011

(54) INSTRUMENTS AND METHODS FOR INSERTING A SPINAL IMPLANT

(75) Inventors: Javier Garcia-Bengochea, Jacksonville, FL (US); Erik J. Wagner, Austin, TX (US); David J. Krueger, Austin, TX (US)

(73) Assignee: Zimmer Spine, Inc., Minneapolis, MN (US)

( * ) Notice: Subject to any disclaimer, the term of this patent is extended or adjusted under 35 U.S.C. 154(b) by 1155 days.

(21) Appl. No.: 10/291,223

(22) Filed: Nov. 8, 2002

(65) Prior Publication Data

US 2003/0135275 A1 Jul. 17, 2003

Related U.S. Application Data

(60) Provisional application No. 60/338,321, filed on Nov. 9, 2001.

(51) Int. Cl.
*A61B 17/70* (2006.01)

(52) U.S. Cl. ..................................................... 606/279

(58) Field of Classification Search .................. 606/99, 606/86, 90, 104, 100, 86 A, 86 R; 623/17.11, 623/17.15, 17.16, 23.5
See application file for complete search history.

(56) References Cited

U.S. PATENT DOCUMENTS

| | | | |
|---|---|---|---|
| 4,743,256 A | 5/1988 | Brantigan | |
| 4,768,787 A | 9/1988 | Shira | |
| 4,834,757 A | 5/1989 | Brantigan | |
| 4,877,020 A * | 10/1989 | Vich | 606/86 |
| 4,878,915 A | 11/1989 | Brantigan | |
| 4,964,641 A | 10/1990 | Miesch et al. | |
| 5,192,327 A | 3/1993 | Brantigan | |
| 5,306,307 A | 4/1994 | Senter et al. | |
| 5,425,772 A | 6/1995 | Brantigan | |
| 5,429,863 A | 7/1995 | McMillin | |
| 5,443,514 A | 8/1995 | Steffee | |
| 5,526,664 A | 6/1996 | Vetter | |
| 5,593,409 A * | 1/1997 | Michelson | 606/247 |
| 5,609,635 A | 3/1997 | Michelson | |
| 5,653,763 A | 8/1997 | Errico et al. | |
| 5,712,919 A * | 1/1998 | Ruhling | 381/316 |
| 5,713,899 A | 2/1998 | Marnay et al. | |
| 5,716,415 A | 2/1998 | Steffee | |
| 5,717,006 A | 2/1998 | Daculsi et al. | |
| 5,769,897 A | 6/1998 | Harle | |
| 5,814,084 A | 9/1998 | Grivas et al. | |
| 5,888,227 A | 3/1999 | Cottle | |
| 5,961,554 A | 10/1999 | Janson et al. | |

(Continued)

OTHER PUBLICATIONS

Office Action issued in U.S. Appl. No. 10/291,245 dated Jun. 6, 2005, Garcia, 5 pages.

(Continued)

*Primary Examiner* — Eduardo C Robert
*Assistant Examiner* — David Comstock
(74) *Attorney, Agent, or Firm* — Sprinkle IP Law Group

(57) ABSTRACT

Instruments of an instrumentation set may be used to prepare a disc space and to insert an implant into the prepared disc space. The instruments may include fixed tip distractors and/or modular tip distractors. The instruments may include a chisel. The chisel may allow simultaneous removal of a desired amount of bone from each of a pair of vertebrae. The instruments may include an implant inserter. The implant inserter may grip sides of an implant. A portion of the implant inserter may fit within grooves of the implant to minimize or eliminate portions of the implant that extend beyond side surfaces of the implant.

14 Claims, 16 Drawing Sheets

U.S. PATENT DOCUMENTS

| | | | |
|---|---|---|---|
| 6,025,538 | A | 2/2000 | Yaccarino, III |
| 6,080,155 | A | 6/2000 | Michelson |
| 6,113,639 | A | 9/2000 | Ray et al. |
| 6,126,689 | A | 10/2000 | Brett |
| 6,143,033 | A | 11/2000 | Paul et al. |
| 6,159,211 | A | 12/2000 | Boriani et al. |
| 6,174,311 | B1 * | 1/2001 | Branch et al. ............... 606/61 |
| 6,200,347 | B1 | 3/2001 | Anderson et al. |
| 6,210,412 | B1 | 4/2001 | Michelson |
| 6,224,631 | B1 * | 5/2001 | Kohrs ................... 623/17.11 |
| 6,241,770 | B1 | 6/2001 | Michelson |
| 6,245,108 | B1 | 6/2001 | Biscup |
| 6,277,149 | B1 | 8/2001 | Boyle et al. |
| 6,290,724 | B1 | 9/2001 | Marino |
| 6,294,187 | B1 | 9/2001 | Boyce et al. |
| 6,319,257 | B1 * | 11/2001 | Carignan et al. ............. 606/99 |
| 6,346,123 | B1 | 2/2002 | McKay |
| 6,468,311 | B2 | 10/2002 | Boyd et al. |
| 6,537,589 | B1 | 3/2003 | Chae et al. |
| 6,638,310 | B2 * | 10/2003 | Lin et al. ................ 623/17.11 |
| 6,719,794 | B2 * | 4/2004 | Gerber et al. ............ 623/17.11 |
| 6,746,454 | B2 * | 6/2004 | Winterbottom et al. ........ 606/99 |
| 7,938,857 | B2 | 5/2011 | Garcia |
| 2003/0139812 | A1 | 7/2003 | Garcia et al. |
| 2003/0139813 | A1 | 7/2003 | Messerli et al. |
| 2008/0015701 | A1 | 1/2008 | Garcia et al. |
| 2008/0195209 | A1 | 8/2008 | Garcia et al. |

OTHER PUBLICATIONS

Office Action issued in U.S. Appl. No. 10/291,245 dated Jan. 10, 2006, Garcia, 6 pages.

Office Action issued in U.S. Appl. No. 10/291,245 dated Sep. 21, 2006, Garcia, 7 pages.

Office Action issued in U.S. Appl. No. 10/291,245 dated May 4, 2007, Garcia, 7 pages.

Office Action issued in U.S. Appl. No. 11/774,340 mailed Jun. 17, 2010, 6 pgs.

Office Action issued in U.S. Appl. No. 11/774,406 mailed Jul. 21, 2010, 6 pgs.

Office Action issued in U.S. Appl. No. 11/774,340 mailed Nov. 22, 2010, 9 pgs.

Notice of Allowance issued in U.S. Appl. No. 11/774,340 mailed Mar. 2, 2011, 5 pgs.

Product Brochure, Spinal Concepts, "Cadence™ Vue, The Clear Choice," Jul. 2003, 2 pages.

Product Brochure, Synthes, "Contact Fusion Cage Surgical Technique," SYNTHES Spine 2002, 18 pages.

Product Brochure, Synthes Spine, "Vertebral Spacer—TR," SYNTHES Spine 2002, 2 pages.

Product Brochure, Stryker Spine, "AVS™ TL PEEK Spacer, Comprehensive System Overview," 2006 Stryker, 7 pages.

Product Brochure, Stryker Spine, "Position Matters, AVS™ TL PEEK Spacer System," 2005 Stryker, 2 pages.

Product Brochure, DePuy Spine, a Johnson & Johnson Company, DEVEX™ System, 2003 DePuy Spine, Inc., 4 pages.

Product Brochure, DePuy AcroMed™, "Lumbar I/F Cage System Surgical Technique," 2001 DePuy AcroMed, Inc., 17 pages.

Product Brochure, Stryker Spine, "Design Matters, AVS™ PL Spacer System," 2004 Stryker, 2 pages.

1st International Carbon Fibre Interbody Fusion Spine Meeting, "Indications, Pitfalls, Complications and Experiences," Munich, Germany, Nov. 7-8, 1997, 34 pages.

Product Brochure, DePuy Spine, a Johnson & Johnson Company, "Jaguar™ Lumbar I/F Cage System Made with CFRP, The Fusion of Power and Performance," 2003 DePuy Spine, Inc., 5 pages.

Product Brochure, DePuy Spine, a Johnson & Johnson Company, "Concorde™ Implants," 2005 DePuy Spine, Inc., 5 pages.

Office Action issued in U.S. Appl. No. 11/774,406, mailed Apr. 4, 2011, 8 pages.

* cited by examiner

INSTRUMENTS AND METHODS FOR INSERTING A SPINAL IMPLANT

PRIORITY CLAIM

This application claims priority to U.S. Provisional Application No. 60/338,321 entitled "Spinal Implant", filed Nov. 9, 2001. The above-referenced provisional application is incorporated by reference as if fully set forth herein.

BACKGROUND OF THE INVENTION

1. Field of the Invention

The present invention generally relates to the field of instruments for preparation of a space and insertion of bone implants into a patient. The present invention also generally relates to instruments and methods for preparing disc spaces and inserting spinal implants between vertebrae.

2. Description of Related Art

An intervertebral disc may degenerate. Degeneration may be caused by trauma, disease, and/or aging. An intervertebral disc that becomes degenerated may have to be partially or fully removed from a spinal column. Partial or full removal of an intervertebral disc may destabilize the spinal column. Destabilization of a spinal column may result in alteration of a natural separation distance between adjacent vertebrae. Maintaining the natural separation between vertebrae may prevent pressure from being applied to nerves that pass between vertebral bodies. Excessive pressure applied to the nerves may cause pain and/or nerve damage. During a spinal fixation procedure, a spinal implant may be inserted within a space created by the removal or partial removal of an intervertebral disc between adjacent vertebrae. The spinal implant may maintain the height of the spine and restore stability to the spine. Bone growth may fuse the implant to adjacent vertebrae.

A spinal implant may be inserted during a spinal fixation procedure using an anterior, lateral, or posterior spinal approach. A discectomy may be performed to remove or partially remove a defective or damaged intervertebral disc. The discectomy creates a disc space for a spinal implant. The amount of removed disc material may correspond to the size and type of spinal implant to be inserted.

Spinal surgery may be complex due in part to the proximity of the spinal cord and/or the cauda equina. Preparation instruments and spinal implants may need to be carefully inserted to avoid damage to nerve tissue. Alignment and spacing of a spinal implant that is to be inserted into a patient may be determined before surgery. Achieving the predetermined alignment and spacing during surgery may be important to achieve optimal fusion of adjacent vertebrae.

Bone graft and/or bone implants may be used to promote bone growth that will fuse vertebrae together. Bone graft may be autogenic bone, allogenic bone, synthetic material, xenogenic bone or combinations thereof. Autogenic bone is bone obtained from another location of a patient. Allogenic bone is bone derived from the same species as the patient. Xenogenic bone is bone derived from a species other than that of the patient. Implants may be formed of metal, polymers, ceramics, autogenic bone, allogenic bone, xenogenic bone, or combinations thereof.

U.S. Pat. No. 5,814,084 to Grivas et al., which is incorporated by reference as if fully set forth herein, describes diaphysial cortical bone dowels. The dowels are obtained from transverse plugs across the diaphysis of long bones. The natural intramedullary canal of the source bone may form a cavity through the dowel perpendicular to the length of the dowel.

U.S. Pat. No. 6,025,538 to Yaccarino, III, which is incorporated by reference as if fully set forth herein, describes a composite allograft bone device. A first bone component is formed with a plurality of grooves. A second bone component is formed with a plurality of protrusions that mate with the grooves of the first bone component. A pin positioned at an oblique angle through the bone components joins the components together to form the composite allograft bone device.

U.S. Pat. No. 6,143,033 to Paul et al., which is incorporated by reference as if fully set forth herein, describes an allogenic intervertebral implant. The intervertebral implant is an annular plug that conforms in size and shape to end plates of adjacent vertebrae. Top and bottom surfaces of the implant have teeth to resist expulsion and to provide initial stability.

SUMMARY OF THE INVENTION

A spinal implant may be used to provide stability and promote fusion of adjacent vertebrae. The implant may be used in conjunction with a spinal stabilization device such as a bone plate or rod-and-fastener stabilization system. The implant may be formed of two or more pieces that are attached together. The implant may establish a desired separation distance between vertebrae. The implant may promote bone growth between adjacent vertebrae that fuses the vertebrae together.

In some implant embodiments, the implants may be made of bone. In some embodiments, bone pieces that form the implant may include rotational dovetails so that a dovetail joint is formed when the pieces are connected together. The dovetail joint may inhibit separation of the bone pieces. The dovetail joint may inhibit lateral movement of the bone pieces relative to each other. A pin may be used to join the pieces together to inhibit rotation of the pieces relative to each other.

In some implant embodiments, a first implant piece may include a protrusion. A second implant piece may include a complementary groove. The pieces may be joined in an interlocking engagement to align the pieces and inhibit axial movement of the pieces relative to each other. A fastener may be placed into openings in the pieces to join the pieces together and form the implant. The fastener may inhibit movement of the pieces relative to each other. The use of a protrusion on a first implant piece and a groove on a second implant piece may simplify manufacturing procedures and time needed for forming spinal implants. Simplified manufacturing procedures may reduce manufacturing errors that result in loss of useable bone.

In some implant embodiments, implants may be formed of three or more pieces. Two pieces are outer pieces that have surfaces for contacting vertebrae during use. Other pieces are middle pieces that allow an implant of a desired height to be formed. Mating surfaces of two pieces that are to be joined together may include a single protrusion and a single groove. After the pieces are joined together and aligned, a fastener may be placed into openings to join the pieces together and form the implant. In some implant embodiments, more than one fastener may be used to join implant pieces together.

Openings in implant pieces for a fastener that joins implant pieces together may be formed so that an axis of the opening is substantially normal to an interface between implant pieces (e.g., within about ±4° of being at 90°). Using openings that are normal to the interface between implant pieces may simplify formation of the openings and reduce useable bone loss due to fracturing of bone pieces caused by forming angulated openings.

In some implant embodiments, fasteners that join implant pieces together are dowels that are press fit into openings in the implant pieces. In other embodiments, fasteners may be, but are not limited to, screws, snap-locks, or barbs. In some embodiments, implant pieces may be joined together by adhesive and/or press fit connections.

In an implant embodiment, the implant includes channels along sides of the implant. An implant inserter may grasp the channels to allow for insertion of the implant into a prepared disc space. The implant channels provide a large surface area for contact between the implant and the implant inserter. The implant channels may be deep enough so that outer surfaces of the implant inserter adjacent to the implant are slightly recessed relative to side surfaces of the implant when the implant inserter holds the implant. The arrangement of the implant inserter relative to the implant allows for an opening between bones that are to be fused together by the implant to be formed to a width that is substantially the same as the width of the implant.

Implants may be constructed of any biocompatible materials sufficiently strong to maintain spinal distraction. Implants may be, but are not limited to, allograft bone, xenograft bone, autograft bone, metals, ceramics, polymers, or combinations thereof. If the implant is not made of bone, surfaces of the implant that contact bone may be treated to promote fusion of the implant to the bone. The treatment may be, but is not limited to, applying a hydroxyapatite coating on contact surfaces, providing a titanium plasma spray on contact surfaces, or texturing the contact surfaces by scoring, peening, implanting particles in the surfaces, or otherwise roughening the surfaces.

In some embodiments, the implant may include an opening that extends through a height of the implant. The opening may have a regular shape or an irregular shape. Bone graft may be placed in the opening. The bone graft may be autogenic bone graft, allogenic bone graft, xenogenic bone graft, and/or synthetic bone graft.

Some implant embodiments may be constructed from allogenic bone, such as cortical bone from a femur, tibia, or other large bone. In some embodiments, an implant may be formed from a single piece of allograft bone that is cut to a desired shape.

Desired dimensions of a bone implant may exceed the dimensions of an implant that may be formed using a single piece of available bone. Two or more pieces of bone may be used to form an implant of a desired length, width, and height. Using pieces of bone may allow for efficient use of available bone. Using pieces of bone may allow for formation of an implant that has greater strength than an implant formed of a single piece of bone.

Bone pieces that are used to form an implant may be formed with joints. The joints may be male or female dovetail joints. The joints may be rotational joints that connect with a mating joint when the pieces are rotated relative to each other. The joints may hold the pieces together and inhibit axial displacement of the pieces relative to each other. A fastener may couple the pieces together to inhibit axial and/or rotational movement of the pieces relative to each other.

In some embodiments, bone pieces that are joined together to form an implant are processed in a frozen state. Care may need to be taken during thawing of the implant to ensure that a fastener or fasteners of the implant remain securely connected to the implant. In some embodiments, bone pieces that are joined together to form an implant are processed in a freeze-dried state. Using bone in a freeze-dried state advantageously allows all pieces of resulting implant to remain securely connected together when the implant is reconstituted before insertion into a patient.

To form an implant from implant pieces, upper and lower surfaces of individual pieces may be machined to have desired maximum lengths, widths, and heights. Sides of the pieces may be machined so that the assembled implant will have side implant channels when assembled. An appropriate joint may be formed in a surface of the implant piece that will mate with another implant piece. In some implant embodiments, openings are formed in the implant pieces. The openings may be formed so that an axis of the opening is substantially normal to a surface of the implant piece that will mate to another implant piece. The individual pieces are joined together. A fastener is used to join the pieces together.

After the pieces are joined together, the implant may be machined to form teeth in surfaces of the implant that contact vertebrae. Also, the implant may be machined so that an anterior height of the implant is different than a posterior height of the implant. An implant with different anterior and posterior heights may allow the implant to establish a desired lordotic angle between adjacent vertebrae.

Instruments may be used to prepare a space for an implant. An instrument may be used to insert an implant in a prepared space. Instruments may be supplied to a surgeon or surgical team in an instrument set. The instrument set may also include one or more implants that can be inserted into a patient during an insertion procedure. Implant may be provided in various sizes and with various lordotic angles so that the implant or implants installed in the patient suit the needs of the patient.

An instrumentation set may include distractors. In some embodiments, the distractors may be fixed tip distractors. In some embodiments, the distractors may be modular tip distractors. A shaft and a handle may be removed from a modular tip distractor to leave only the modular tip distractor in a disc space. Leaving only a modular tip distractor in a disc space may create more room for visualization and maneuverability during an implant insertion procedure.

An instrumentation set may include a chisel. The chisel may form grooves in vertebral surfaces. The grooves may be sized to accept a portion of an implant that is to fuse vertebrae together. The chisel may simultaneously form channels in both vertebra during use.

An instrumentation set may include an implant inserter. The implant inserter may grasp side walls of an implant. Grasping side walls of the implant may allow for removal of the implant inserter from the implant inserter without the application of significant rotational forces to the implant. The implant inserter may have a low profile that allows for visualization of the implant and surrounding area during insertion of the implant.

BRIEF DESCRIPTION OF THE DRAWINGS

Advantages of the present invention will become apparent to those skilled in the art with the benefit of the following detailed description of embodiments and upon reference to the accompanying drawings in which.

Figure 1:
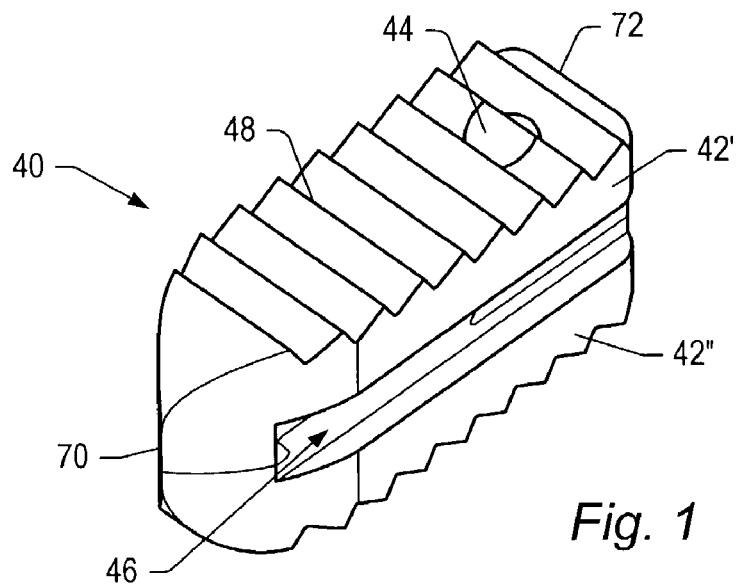
FIG. 1 depicts a perspective representation of an embodiment of an implant.

While the invention is susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION OF EMBODIMENTS

FIGS. 1-13 show embodiments of implants 40 and portions of implants that may be used to promote bone fusion. Implants 40 may be spinal implants, such as, but not limited to, posterior lumbar interbody fusion (PLIF) spinal implants. A spinal implant may establish a desired separation distance between adjacent vertebrae. In some implant embodiments, implants have surfaces made of bone or bone growth promoting material (e.g., hydroxyapatite or titanium plasma spray) that promotes fusion of the implants to vertebrae. In some embodiments, implants may include openings. The openings may be packed with bone graft or other bone growth material that promotes bone growth from vertebrae into the implant to fuse the implant to the vertebrae.

As depicted in FIG. 1, implant 40 may include members 42, fastener 44, side grooves 46, and serrations or ridges 48. An implant may include two or more members 42. Members 42 may be joined together to form implant 40. In some embodiments, members 42 may be joined together by a rotational dovetail joint. The rotational dovetail joint may inhibit separation and axial movement of members 42 relative to each other. Fastener 44 may be press fit into an opening that extends through first member 42' and into an opening in second member 42". In some embodiments, fastener 44 may inhibit rotation of first member 42' relative to second member 42".

In some embodiments, a joint of the first member may allow the first member to fully rotate (i.e., through 360°) in a clockwise or counterclockwise direction when coupled to a corresponding mating joint in the second member. In some embodiments, a range of motion and/or a direction of motion may be limited. For example, in an embodiment, a joint of the first member can be rotated 45° in a clockwise direction when coupled to a corresponding mating joint of a second member. Surface contact between the first member and the second member inhibits rotational movement beyond the 45° limit. Surface contact between the first member and the second member inhibits initial counterclockwise rotation of the first member relative to the second member. Other embodiments may have different angular rotation limits (e.g., 30° or 60°) or other angular direction limits. In some embodiments, a first member may rotate relative to the second member for only a limited range of angular rotation in either a clockwise or a counterclockwise direction.

Figure 2:
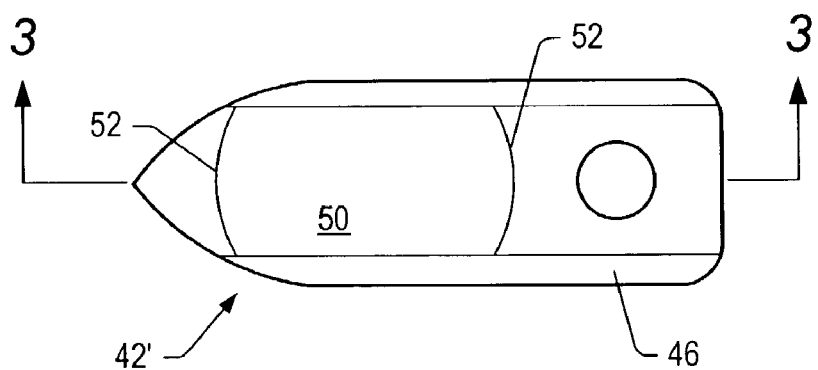
FIG. 2 depicts a plan view of an embodiment of an implant member that emphasizes a surface of the implant member having a male joint.
Figure 3:
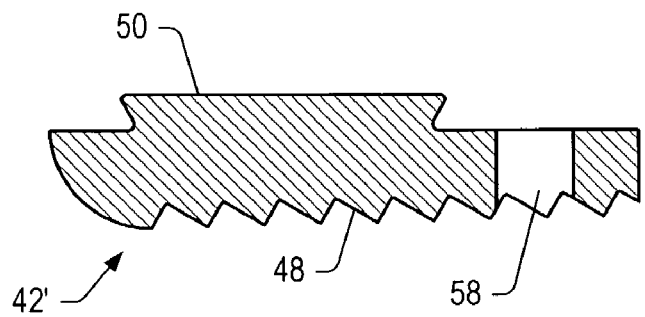
FIG. 3 depicts a cross-sectional representation of an embodiment of an implant member that has a male joint taken substantially along line 3-3 of FIG. 2.

FIG. 2 depicts a plan view of an embodiment of member 42' that emphasizes a surface of the member that has male dovetail 50. Male dovetail 50 may include arced surfaces 52. Arced surfaces 52 may be circular arcs that are concentric. FIG. 3 depicts a cross-sectional view of an embodiment of member 42' having male dovetail 50.

Figure 4:
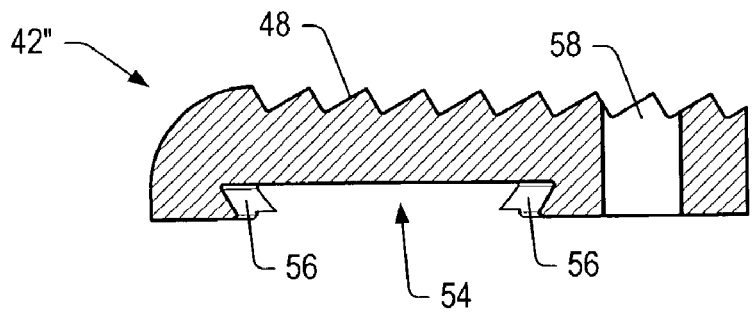
FIG. 4 depicts a cross-sectional representation of an embodiment of an implant member that has a female joint.

FIG. 4 depicts a cross-sectional view of member 42" that has female dovetail 54. Female dovetail 54 may include arced surfaces 56. Arced surfaces 56 may be circular arcs that have are concentric.

Male dovetail 50 of member 42' (shown in FIG. 3) may be placed in female dovetail 54 of member 42" (shown in FIG. 4), with a long axis of member 42' oriented substantially perpendicular to a long axis of member 42". Member 42' may be rotated to a position substantially parallel to member 42". When members 42', 42" are properly oriented, openings 58 in the members may align with each other. Fastener 44, depicted in FIGS. 1 and 5, may be placed into openings 58 to inhibit further rotation of member 42' relative to member 42". Openings 58 may be formed in members 42', 42" before or after the members are joined together using female dovetail 54 and male dovetail 50 of the members. In some embodiments, an opening in a member may be a blind opening (i.e., an opening that does not extend completely through the member).

Figure 5:
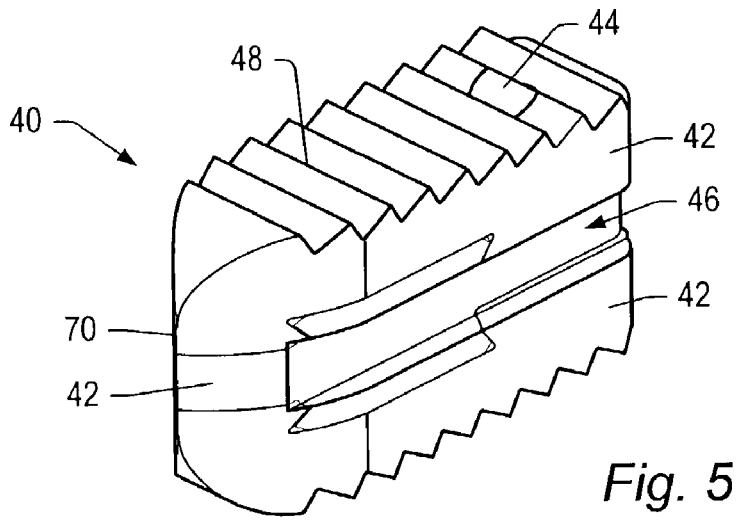
FIG. 5 depicts an embodiment of an implant formed of three implant members.
Figure 6:
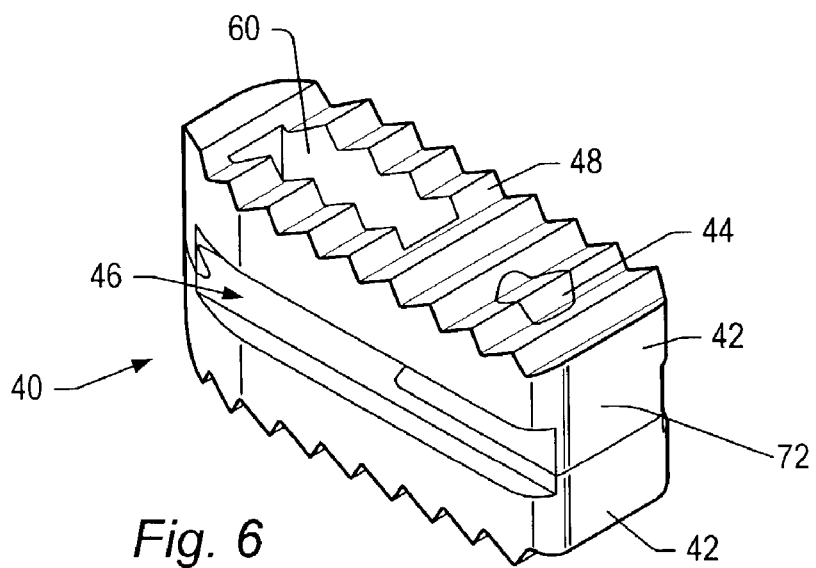
FIG. 6 depicts an embodiment of an implant that includes a passage through the implant.

In some embodiments, fastener 44 may be press fit into openings in members 42 to join the members together to form implant 40, as depicted in FIGS. 5 and 6. In other embodiments, the fastener may be another type of fastener, including, but not limited to, a screw, a snap lock connector, a barbed connector, and/or adhesive. The fastener may be made of the same material as the implant members (e.g., bone). In other embodiments, the fastener may be made of a different material than the implant members. The fastener or a portion of the fastener may include material that promotes osseointegration of the fastener and the implant with vertebrae. The fastener or a portion of the fastener may be made of a material that is absorbable in the body of a patient. After absorption, bone may grow in place of the bioabsorbable material to facilitate fusion of the implant to bone of a patient.

In some embodiments, an implant may be formed of three or more members. FIG. 5 depicts an embodiment of implant 40 formed of three members 42. In some embodiments, four, five, or more members may be joined together to form an implant. An implant formed from two or more members may have a larger height than an implant formed from a single piece of bone. The ability to form an implant from two or more members may allow for the formation of an implant of a desired height while maximizing the use of available donor bone.

Rotational dovetail joints may connect members together. Male and female joints may be formed in pieces that form the implant. For example, in an embodiment of a three-member implant, male joints are formed in outer members of the implant, and an interior member is formed with two female joints. In another embodiment of a three-member implant, an interior member is formed with a male joint and a female joint, one of the outer members has a male joint, and the other outer member has a female joint. In another embodiment of a three-member implant, female joints are formed in outer members, and an interior member is formed with two male joints.

In some implant embodiments, an implant may have a passage or passages from one side of the implant to an opposite side of the implant. FIG. 6 depicts implant 40 that includes passage 60 through the implant. Passage 60 may be formed in members 42 before or after the members are joined together. Passage 60 may have any desired cross-sectional shape. The passage cross-sectional shape may be, but is not limited to, circular, oval, square, rectangular, or irregular. Bone growth material (e.g., autogenic bone graft, allogenic bone graft, xenogenic bone graft, or synthetic bone graft) may be placed in the passage or passages to facilitate spinal fusion.

In some implant embodiments, bone may be used to form an implant. Portions of the bone used to form the implant may be cortical bone. The cortical bone may provide strength to the implant. In some implant embodiments, the bone used to form an implant may be processed in a frozen state. In some implant embodiments, bone used to form an implant may be processed in a freeze-dried state.

In some implant embodiments, the implant and/or outer surfaces of the implant that contact a vertebra may be made of a material other than bone. The surface that contacts the vertebra may be treated to enhance osseointegration of the implant with the vertebra. The surface may include protrusions that extend into the vertebra. The surface may include a hydroxyapatite coating, a titanium plasma spray coating, and/or texturing. Texturing may be used to modify the surface of an implant to reduce expulsion and provide stability. Texturing may be provided by many different methods, such as, but not limited to, sanding the surface, forming grooves within the surface, shot peening the surface, scoring the surface using an electrical discharge process, and/or embedding hard particles within the surface. Texturing may also be formed in outer surfaces of implants formed of bone.

Implants may be constructed of biocompatible material sufficiently strong to maintain bone separation. Implant members and/or fasteners may be made of bone or of other material, such as metals, ceramics, polymers, or combinations thereof. Bone used to form an implant may be allogenic bone or xenogenic bone. In some embodiments, a portion or portions of an implant may be autogenic bone. In some embodiments, bone, or portions of bone, used to form an implant may be demineralized. An implant, or a portion of an implant, may be made of a bioabsorbable material. For example, portions of an implant may be made of a polyanhydride, an alpha polyester, and/or a polylactic acid-polyglycolic acid copolymer.

In some embodiments, an implant may be a single-member implant constructed from bar stock or formed from moldable material of suitable strength to withstand pressure within a normal human spine. For example, a single-member implant may be constructed from metals including, but not limited to, titanium, titanium alloys, and medical grade stainless steel. A single-member implant may be molded or cut from materials including, but not limited to, polyether ether ketone (PEEK), carbon fiber reinforced PEEK, and other polymers.

Figure 7:
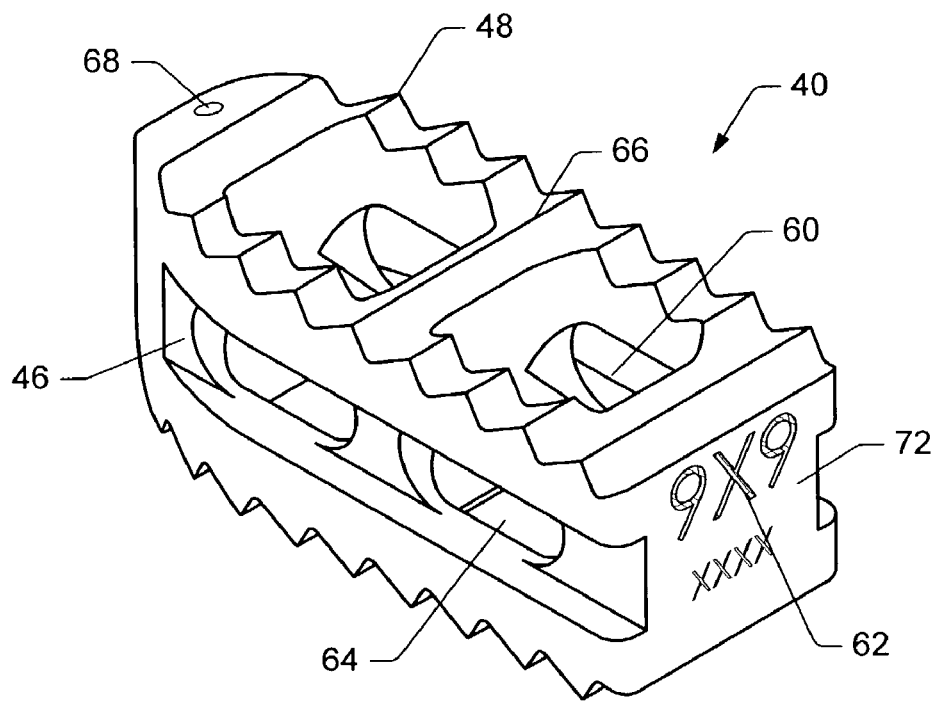
FIG. 7 depicts a perspective view of an embodiment of a single-member implant.

FIG. 7 depicts an embodiment of single-member implant 40. Implant 40 may include indicia 62. Indicia 62 may identify size, shape, and/or orientation of implant 40. Implant 40 may include one or more passages 60 and/or one or more passages 64. In an embodiment, passage 64 may be substantially perpendicular to passage 60. Passages 60, 64 may have any desired cross-sectional shape. Cross-sectional shapes of passages 60, 64 may be, but are not limited to, circular, oval, square, rectangular, and/or irregular. Bone growth material (e.g., autogenic bone graft, allogenic bone graft, xenogenic bone graft, or synthetic bone graft) may be placed in the passage or passages to facilitate spinal fusion.

In some embodiments, passages 60, 64 may be positioned at locations to promote overall strength of implant 40. In some embodiments, rib 66 may separate a first passage 60 from a second passage 60 and/or a first passage 64 from a second passage 64. Rib 66 may provide strength to implant 40 such that a shape of the implant is maintained under pressure exerted by spinal compression. In an embodiment, a single-member implant formed from PEEK may include at least one supporting rib 66. In some embodiments, the use of rib 66 with proper placement of passages 60, 64 may allow the use of virgin PEEK, as opposed to PEEK that includes carbon fiber or other type of reinforcement material.

Figure 8:
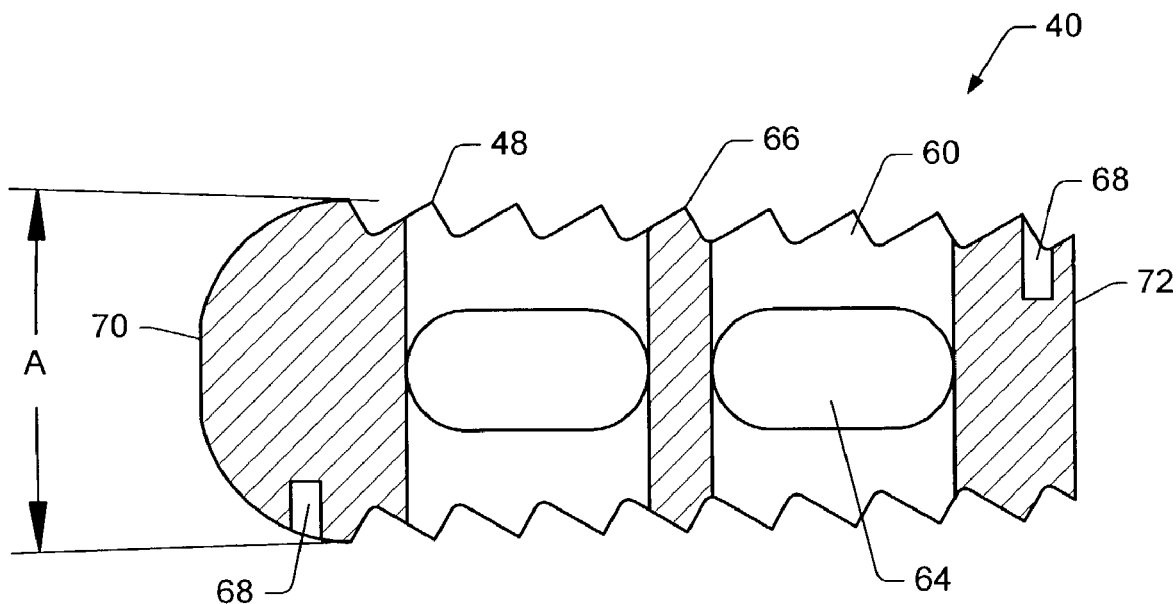
FIG. 8 depicts a cross-sectional representation of a single-member implant.

In some cases, X-rays may be used to monitor spinal fusion in a patient. Some implant embodiments (e.g., PEEK implants) are substantially transparent to X-rays. X-ray detection of implant 40 formed of X-ray transparent material may be facilitated by including X-ray sensitive material in the implant. FIG. 8 depicts a cross-sectional representation of single-member implant 40 with openings 68 for X-ray sensitive material. For example, tantalum wire (e.g., 1 mm in length) may be inserted into one or more openings 68 of implant 40 before implantation. In some embodiments, X-ray sensitive material may be located near an anterior end of the implant adjacent to a caudal (or cephalic) surface of the implant. X-ray sensitive material may also be located near a posterior end of the implant adjacent to a cephalic (or caudal) surface of the implant. The use of X-ray sensitive material near anterior/posterior and caudal/cephalic surfaces may allow the position of an implant to be visualized using X-ray imaging.

Bone growth that fuses vertebrae together through an implant may be monitored subsequent to an implant insertion procedure. Bone growth in an implant that is not X-ray transparent (e.g., a metallic implant) may be monitored utilizing passages 64. Passages 64 may allow passage of X-rays through the implant so that an X-ray image taken indicates the presence, absence, and/or density of bone in passages of the implant.

A member of an implant may be formed using computer numerical control (CNC) processing equipment. An outer surface of material that is to be formed into a member may be processed to form the general plan view shape of the implant. In some embodiments, sides of the material may be processed so that channels are formed in the implant when the members are joined together. Channels may be used by certain types of implant inserters. In other embodiments, implants may not include channels. A male joint and/or a female joint may be formed in the member. An opening for a fastener may be formed in the member. Separately forming the implant members may minimize loss of bone should one of the members break or fracture during processing, or should an error occur in the processing instructions supplied to the processing equipment. In some embodiments, pieces of material may be joined together prior to shaping the material to form a desired implant shape.

For an implant embodiment that includes a rotational dovetail joint, the members may be joined together by placing a male joint in a female joint and rotating the members after formation of each member of an implant. A fastener may be press fit into the implant after the members are joined together. In other embodiments, a fastening system other than a press fit fastener may be used to join the members together. For example, the members may be joined together using a screw, snap lock connector, barbed connector, and/or adhesive. The adhesive may be, but is not limited to, a cyanoacrylate, a dental resin cement, an epoxy-based compound, a glass ionomer cement, polymethyl methacrylate, and/or inorganic bonding agents such as zinc carboxylate, zinc phosphate, magnesium phosphate, or other phosphate-based cements.

A resulting implant may be further processed to produce an implant having a desired shape. In some embodiments, a surface or surfaces of the implant that will contact bone may be angled so that the implant will establish a desired orientation between bone pieces that are to be fused together (i.e., a proper lordotic angle). Implants may be formed with different lordotic angles. As shown in FIGS. 5-11, angles between vertebrae contacting surfaces resulting from different heights at anterior ends 70 and posterior ends 72 may range from about 0° (i.e., the implant has substantially parallel vertebrae contact surfaces) to angles of about 20°. The angle may typically range from about 0° to about 6°. Lordotic angle A is depicted in FIG. 8.

In some embodiments, serrations may be formed in surfaces of the implant that will contact bone. In some embodiments, end surfaces of the implant may be machined. For example, tapered and/or arced surfaces may be formed in the implant at an insertion end of the implant. In other embodiments, all processing of the members may be done prior to joining members together so that the implant is fully formed when the members are joined together.

Figure 9:
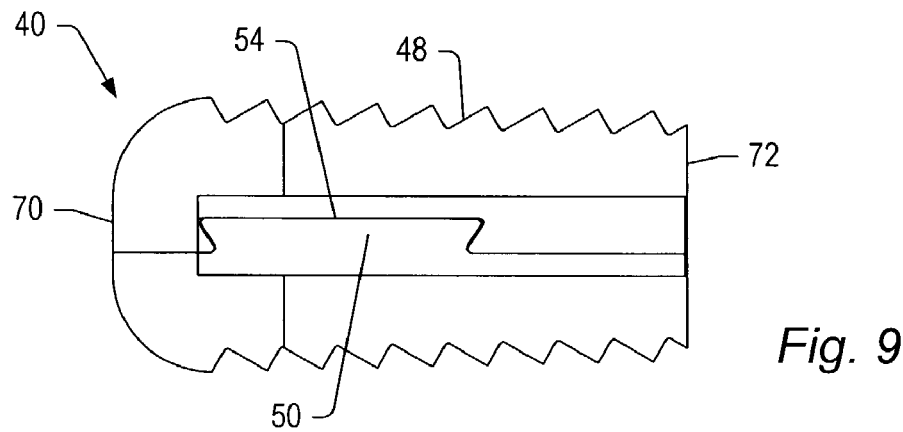
FIG. 9 depicts a front view of an embodiment of an implant.
Figure 10:
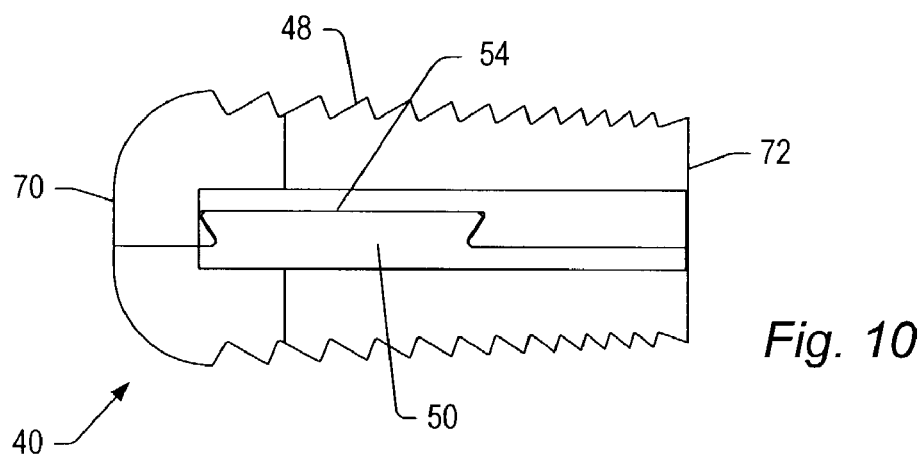
FIG. 10 depicts a front view of an embodiment of an implant.

FIGS. 9 and 10 depict front views of embodiments of implants 40. Implant 40 may include serrations or ridges 48. As shown in FIG. 9, serrations 48 may have substantially constant heights and frequency along a length of implant 40. Alternatively, as shown in FIG. 10, serrations 48 may have varying heights and/or varying frequency along a length of the implant. Heights of the serrations may decrease as the serrations approach posterior end 72 of implant 40. Frequency of the serrations may increase as the serrations approach posterior end 72 of implant 40. Other height and/or frequency patterns may also be used. Serrations 48 may be oriented to inhibit backout of implant 40 after the implant is inserted between bone segments or vertebrae.

Figure 11:
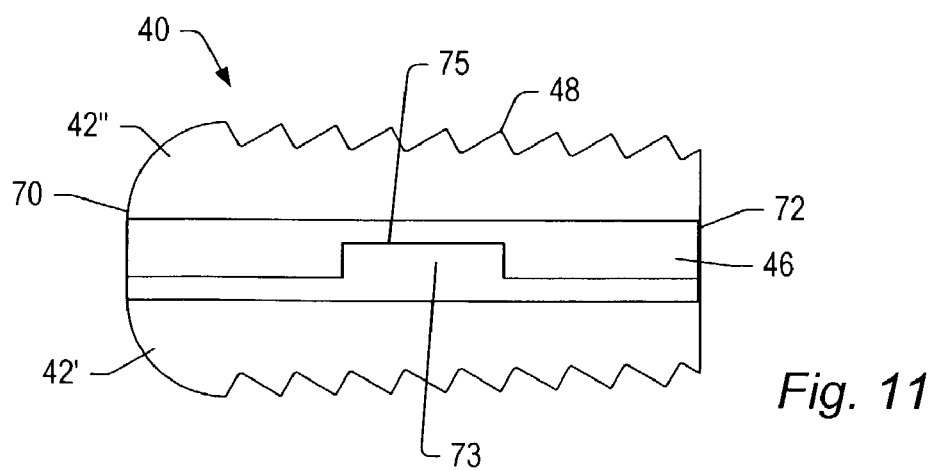
FIG. 11 depicts a front view of an embodiment of an implant.

FIG. 11 depicts a front view of an embodiment of implant 40 with serrations 48. Implant 40 may include members 42', 42". As shown in FIG. 11, member 42' may include protrusion 73. Member 42" may include recess 75. Recess 75 may be complementary to protrusion 73. Recess 75 and protrusion 73 may fit together to align members 42', 42" of implant 40.

Figure 12:
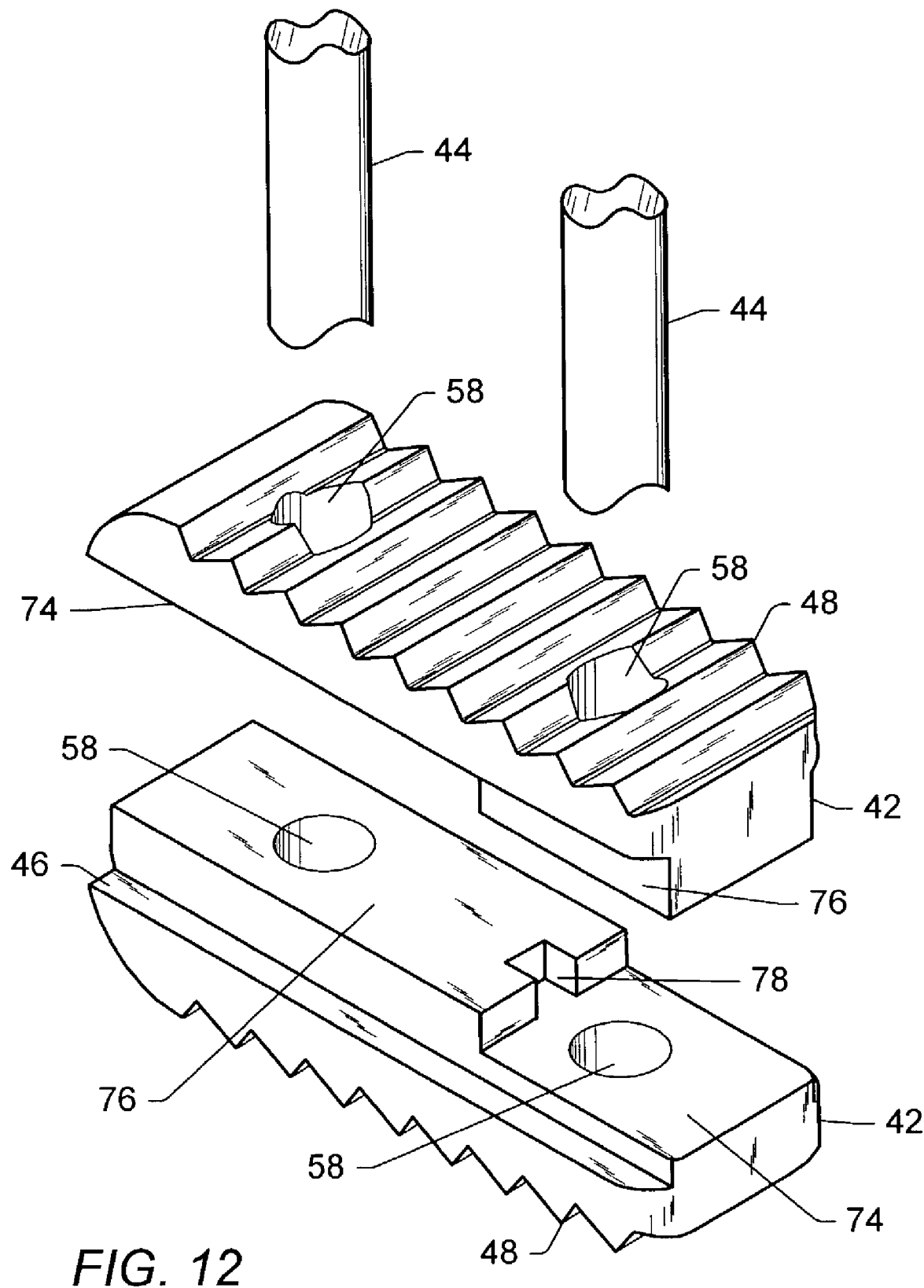
FIG. 12 depicts a perspective exploded view of components of an embodiment of an implant formed of two implant members.

FIG. 12 depicts a perspective exploded view of an embodiment of an implant. The implant of FIG. 12 includes two implant members 42 that are joined together by two fasteners 44. Each implant member 42 may include first portion 74 that is recessed relative to second portion 76. A first portion and a second portion of a first implant member may be complementary to a second portion and a first portion of a second implant member so that the first member and the second member form an implant when joined together. Second portion 76 of a first implant member may fit in first portion 74 of a second implant member, simplifying formation processes used to form the implant members. Simplified formation processes may result in less bone loss due to breakage, fracturing, and/or incorrect cutting during formation of the implant members.

First portions 74 and second portions 76 of implant members 42 may be keyed to facilitate proper positioning and/or alignment of openings 58 in the implant members. For example, one implant member may include keyway 78 and an opposite implant member may include a key that fits within the keyway to properly align the implant members relative to each other. In some embodiments, the implant members may not be keyed. If the implant members are not keyed, and if a separation between first portions and second portions of the implant members is formed substantially midway along lengths of the implant members, then the implant members may advantageously be substantially identical to each other. The use of substantially identical implant members may eliminate the need to form two or more different types of implant members (e.g., male and female). Substantially identical implant members may simplify formation and processing costs and eliminate the need to have multiple types of implant members.

Openings 58 may be formed in implant members 42 so that the openings are substantially normal to interface surfaces of the implant that abut or are adjacent to each other when the implant is assembled. Openings that are substantially normal to interface surfaces between implant members may be easier to form in the implant members and may inhibit fracturing of implant members during formation of the openings. In some embodiments, openings may be formed at angles other than right angles relative to interface surfaces between implant members.

Figure 13:
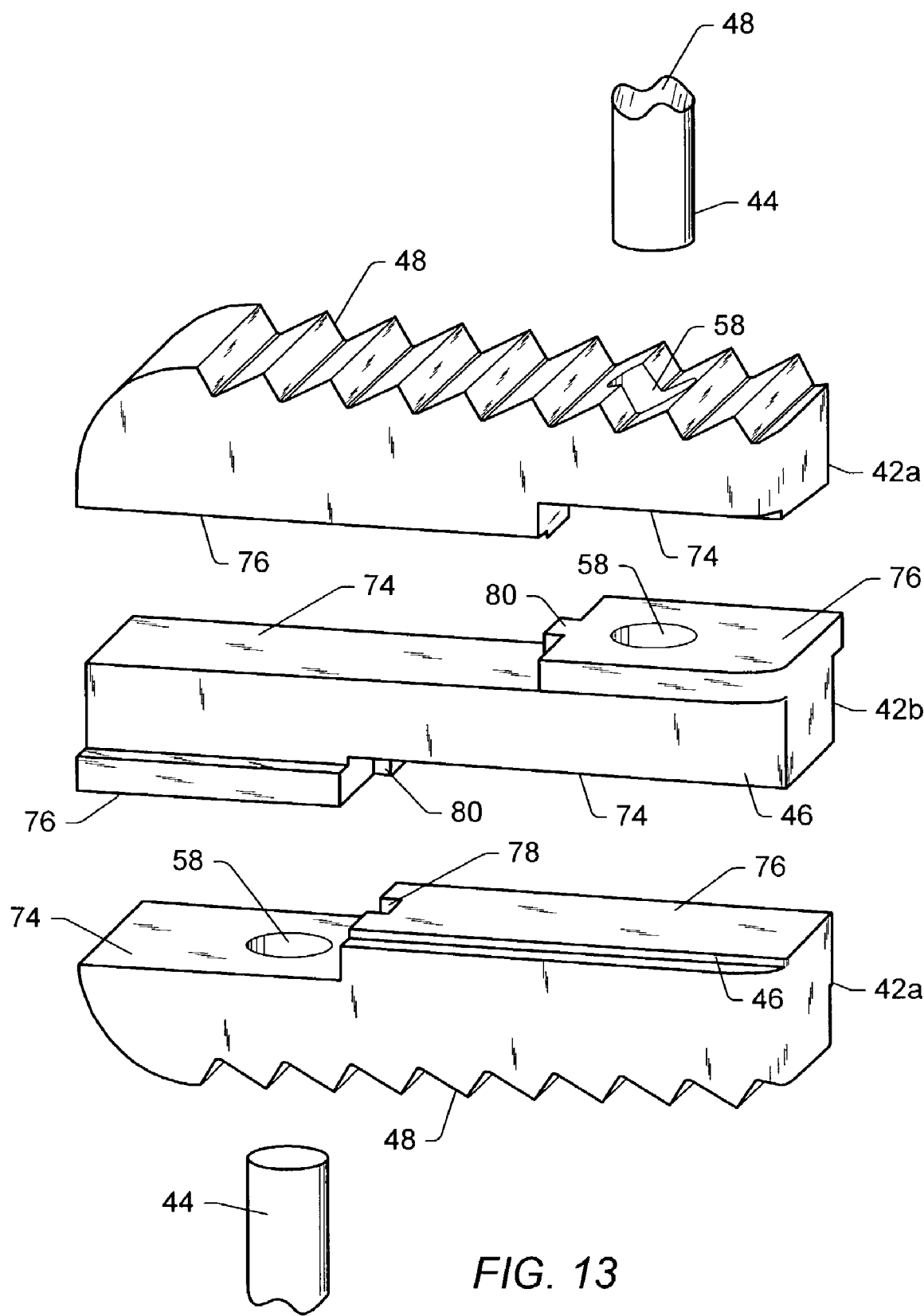
FIG. 13 depicts a perspective exploded view of components of an embodiment of an implant formed of three implant members.
Figure 14:
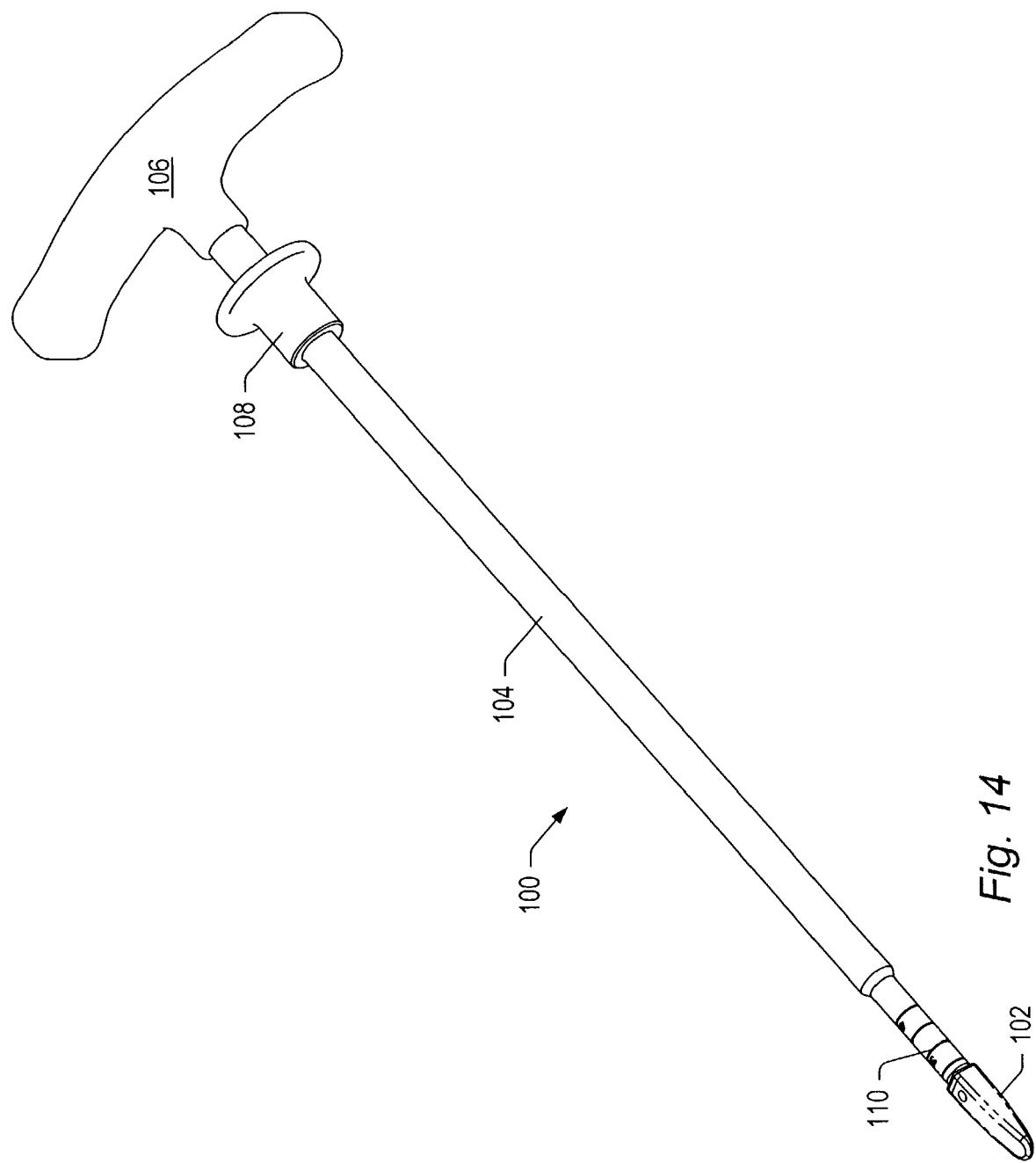
FIG. 14 depicts a perspective view of an embodiment of a fixed tip distractor.

FIG. 13 depicts an exploded view of three implant members 42 that may be joined to form an implant. In other embodiments, four or more implant members may be joined together to form an implant. In the embodiment shown in FIG. 13, each implant member includes first portions 74 and second portions 76. First portions 74 and second portions 76 of implant members 42 are complementary, so that the implant members may be joined together to form an implant. In some embodiments, implant members 42 may be keyed to facilitate proper positioning of the implant members relative to each other before fasteners 44 are used to join the implant members together. In the embodiment depicted in FIG. 13, outer implant members 42a include keyways 78, and interior implant member 42*b* includes keys 80 that are positionable in the keyways. In other embodiments, the implant members may not be keyed.

Outer implant members 42*a* may be formed such that the shapes of the outer members are substantially identical. In some embodiments, heights of outer implant members 42*a* may be different. Complementary steps between a first portion and a second portion may allow implant member interfaces to abut when the implant members are joined together. Substantially identically shaped outer implant members 42*a* may simplify implant formation and processing costs, and may eliminate the need to have more than one type of outer implant member. Substantially identically shaped outer implant members 42*a* may minimize the number of different types of interior implant member 42*b* needed to form implants from multiple implant members. In some embodiments, outer implant members 42*a* may be formed with substantially identical heights, and several interior implant members of different heights may be formed to allow implants of desired heights to be formed from available bone. In some situations, condition and size of available bone may determine the shape and height of implant members that may be formed.

Implant members 42 may include openings 58. In some implant members 42, an opening may be a blind opening. Openings 58 may be formed substantially normal to interface surfaces that abut or are adjacent to another implant member when the implant is assembled. In some embodiments, openings may be angled relative to interface surfaces that abut or are adjacent to another implant member when the implant is assembled.

As shown in FIG. 1, anterior end 70 of implant 40 may include tapered and/or curved surfaces. The tapered and/or curved surfaces may facilitate insertion of implant 40 into a disc space. As shown in FIGS. 8-11, anterior end 70 of implant 40 may be blunt and/or rounded. Posterior end 72 of implant 40 may have a flat surface. A tamp or other insertion instrument may be placed against posterior end 72 during insertion of implant 40 into a disc space using a posterior insertion procedure. In some embodiments, an anterior end may not be tapered and/or curved. The posterior end may be engraved or otherwise marked with indicia to indicate the location of the posterior end and to identify the size and orientation of the part.

Estimated implant heights and estimated amounts of lordotic adjustment may be determined prior to an implant insertion procedure. X-ray and other imaging techniques may be used to estimate heights of implants and desired amounts of lordotic adjustment needed for a particular patient. Implants that will provide the estimated height and lordotic alignment may be provided with an instrumentation set for the implant insertion procedure. Also, implants having greater and lesser heights and/or lordotic adjustment may be provided with the instrumentation set in case conditions during surgery indicate that different implants should be used.

An implant may advantageously be formed of a number of pieces of bone. Using a number of bone pieces may allow for the formation of a strong bone implant of a height that cannot be formed using available bone. Using a number of bone pieces may allow for efficient use of available bone.

In some embodiments, an implant may advantageously include a rotational joint that connects pieces of the implant together. The pieces of the implant may be formed separately to minimize potential bone loss should a problem develop during bone processing. The bone pieces may be coupled together using one or more rotational joints. Each rotational joint may couple two bone pieces together to inhibit separation of the bone pieces and/or lateral displacement of the bone pieces relative to each other.

In some embodiments, an implant may advantageously include a single raised portion and a single recessed portion. Using a single raised portion and a single recessed portion may simplify formation procedures needed to produce implant members. In some embodiments, implant members may be keyed to facilitate proper positioning of the implant members relative to each other.

A fastener or fasteners may be used to inhibit rotational movement of implant members relative to each other after the implant members are coupled to each other. One or more fasteners may also be used to hold implant members together if a rotational joint is not used. Openings in implant members may be formed substantially normal to an interface between the implant members. The openings may have short lengths and may minimally influence the strength of the implant members as compared to slanted openings in implant members. In some implant embodiments, openings may be blind openings. In other implant embodiments, an opening for a fastener may go completely through all implant members that form the implant.

In some implant embodiments, implants may advantageously be shaped to a desired form after an implant is assembled from implant members. In other embodiments, implant members may be shaped to a desired form before joining the implant members together. Texturing and/or serrations or ridges may be formed on surfaces of the implant members that will contact bone to inhibit backout of the implant when the implant is inserted into a patient. In some embodiments, implants may be processed so that posterior sides of the implants have different heights than anterior sides of the implants. Other dimensional characteristics of an implant may also be adjusted to produce an implant having a desired geometry. Further advantages of implants may include that the implants are sturdy, durable, lightweight, simple, efficient, reliable and inexpensive; yet the implants may also be easy to manufacture, install, and use.

An instrumentation set may include instruments that are to be used to insert an implant within a space between two bones of a patient during a bone fusion procedure. The instrumentation set may also include implants that are to be inserted into the patient. Instruments used during a bone fusion procedure may allow a significant portion of positioning and manipulation to be affected from above an incision in a patient. The instruments may allow for insertion of an implant in a simple, efficient, and safe manner. In an embodiment, an implant may be inserted in a disc space between adjacent vertebrae. In other embodiments, an implant may be inserted in a space formed between two portions of a bone to extend the length of the bone. The instruments may allow for a relatively small incision in the patient, yet still allow ample visibility of surgical site, implant, and instruments during the insertion procedure.

An instrumentation set for a spinal implant insertion procedure may include various instruments for distraction, disc preparation, and implantation. The distraction instruments may include fixed tip distractors and/or modular tip distractors. Disc preparation instruments may include, but are not limited to, disc shavers, curettes, rongeurs, chisels, and/or retractors. Implantation instruments may include implant inserters, mallets, tamps, and/or funnels.

During implant insertion, a disc space may be too small to allow for insertion of an implant. Distraction of the vertebrae to a distance slightly less than a height of the implant may facilitate insertion of the disc preparation instruments. FIG.

14 depicts an embodiment of fixed tip distractor 100. Distractor 100 may include tip 102, shaft 104, and removable handle 106. Tip 102 may be fixed to shaft 104. Shaft 104 may include an indention that mates with a detent of handle 106. Handle 106 may include release 108. Moving release 108 upwards may remove a force applied to the detent and allow handle 106 to be removed from shaft 104. In some embodiments, the shaft may include a release and a detent, and the handle may include an indention that couples to the detent. Other types of coupling systems for the handle may also be used. In some embodiments, the handle may be fixed to the shaft. Shaft 104 may include indicia 110 that indicate insertion depth of tip 102 into a disc space.

A distal region of tip 102 may have a cross-sectional shape characterized by a narrow portion and a wide portion. The narrow portion and the wide portion may be substantially perpendicular to each other. A first surface and a second surface of the tip may define the narrow portion. The first surface may taper towards the second surface so that the tip has a varying narrow dimension. In some embodiments, the second surface may also taper towards the first surface. The narrowest portion of the tip may be located distal from a portion of the tip that a shaft of the distractor connects to.

A third surface and a fourth surface of the tip may define the wide portion of the tip. The wide portion may be substantially constant along a length of the tip. The wide portion may be the desired separation distance to be established by the distractor between adjacent vertebrae. Edges of the tip between the first surface and the third surface, and between the first surface and the fourth surface, may be rounded to facilitate rotation of the tip when the tip is inserted between vertebrae. Edges of the tip between the second surface and the third surface, and between the second surface and the fourth surface, may also be rounded to facilitate rotation of the tip when the tip is inserted between vertebrae.

Handle 106 may be a "T" shaped handle. When handle 106 is attached to shaft 104, the handle may be substantially parallel to the wide dimension of tip 102. Handle 106 may be oriented perpendicular to a patient's spinal column. A narrow portion of tip 102 may be inserted into a disc space formed by a discectomy. Handle 106 may be rotated approximately 90° so that the handle is aligned with the spinal column. When handle 106 is aligned with the spinal column, the wide portion of the tip may establish a desired separation distance between vertebrae. Handle 106 may be removed from shaft 104 after the vertebrae are distracted.

Figures 15, 16:
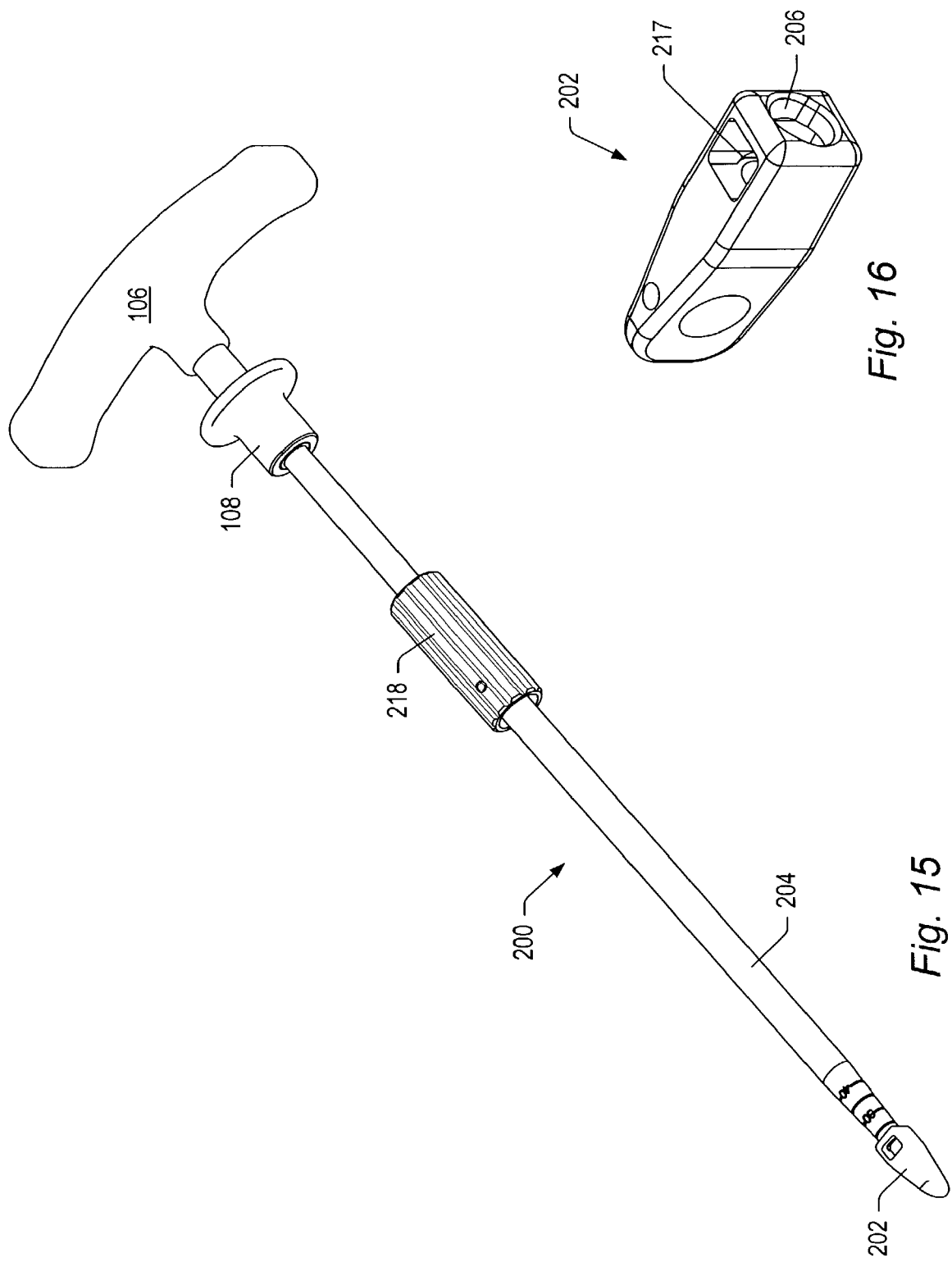
FIG. 15 depicts a perspective view of an embodiment of a modular tip distractor.
FIG. 16 depicts a perspective view of an embodiment of a modular tip of a modular tip distractor.

In an embodiment, a distractor may be a modular tip distractor. FIG. 15 depicts an embodiment of assembled modular tip distractor 200. Modular tip distractor 200 may include modular tip 202, shaft 204, and handle 106. FIG. 16 depicts an embodiment of modular tip 202. Modular tip 202 may include opening 206 that accepts an end of shaft 204. In some embodiments, opening 206 may have an oval cross-sectional shape that allows for rotation of the tip when a shaft having a substantially complementary shape is inserted into the opening. In some embodiments, opening 206 may have a square, rectangular, hexagonal or other non-circular cross-sectional shape that allows for rotation of the tip when a shaft having a substantially complementary shape is inserted into the opening. Handle 106 may be attached and released from shaft 204 in the same manner as described above for the fixed tip distractors. In some embodiments, handle 106 may be affixed to shaft 204.

Figure 17:
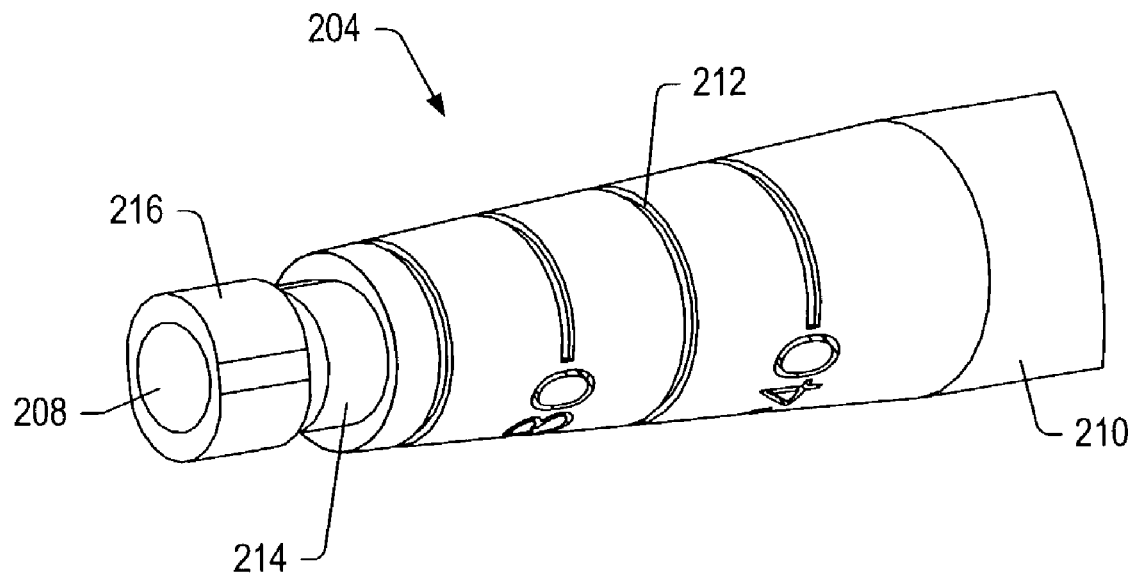
FIG. 17 depicts a perspective view of an embodiment of an end portion of a shaft for a modular tip distractor when the shaft is in an unreleased position.
Figure 18:
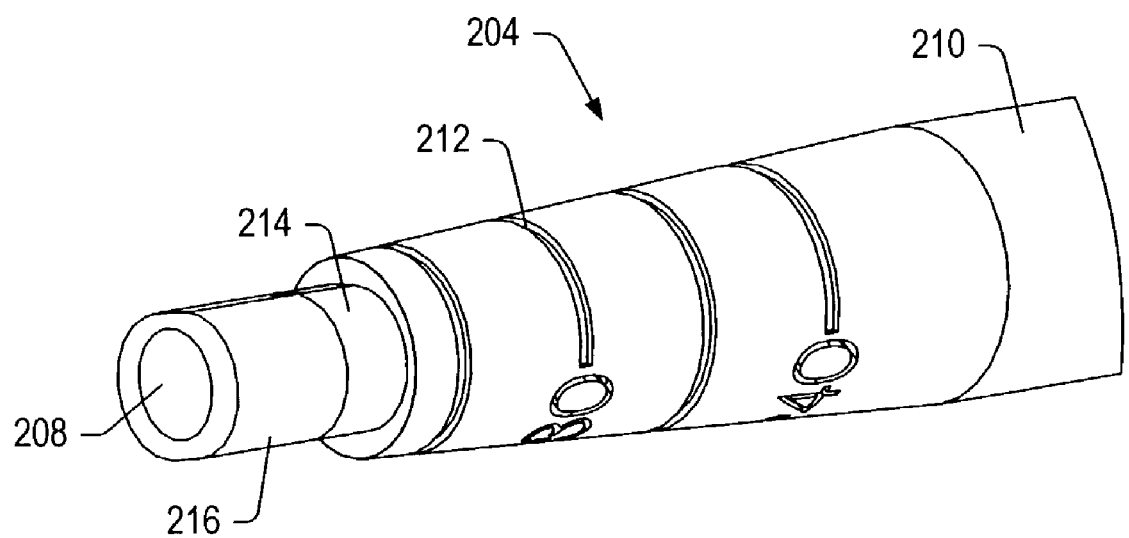
FIG. 18 depicts a perspective view of an embodiment of an end portion of a shaft for a modular tip distractor when the shaft is in a released position.

FIGS. 17 and 18 show portions of shaft 204. Shaft 204 may include inner shaft 208 and outer shaft 210. Outer shaft 210 may include indicia 212 that indicate insertion depth of a modular tip coupled to shaft 204 into a disc space. Portion 214 of outer shaft 210 may have a cross-sectional shape that is substantially the same as, but slightly smaller than the shape of an oval opening in a modular tip. End 216 of inner shaft 208 may have the same cross-sectional shape as outer shaft portion 214. Inner shaft end 216 may be a collar that is coupled to cylindrical inner shaft 208. A modular tip may be coupled to outer shaft portion 214 when inner shaft end 216 is aligned with outer shaft portion 214 as depicted in FIG. 18. When inner shaft end 216 is aligned with outer shaft portion 214, the inner shaft end may be inserted through the oval opening in the modular tip into cavity 217 (shown in FIG. 16) in the modular tip. Inner shaft end 216 may be aligned with outer shaft portion 214 by rotation of gripping member 218 (shown in FIG. 15). When gripping member 218 is released, the gripping member may move to an initial position and rotate inner shaft 208 so that inner shaft end 216 rotates to a position that inhibits removal of the modular tip from outer shaft portion 214. When gripping member 218 is released, inner shaft end 216 may be in a position similar to the position indicated in FIG. 17.

Gripping member 218 may include an internal spring attached to inner shaft 208. The spring may bias inner shaft end 216 to the position shown in FIG. 17 when gripping member 218 is released. The spring may be a torsion or coil spring positioned around inner shaft 208. The spring may be attached to gripping member 218, rotated one or more turns, and attached to inner shaft 208. When a user grasps gripping member 218 and rotates the gripping member, inner shaft 208 may be rotated so that inner shaft end 216 is in the position shown in FIG. 18. When in this position, shaft 204 may be removed from the modular tip. Releasing gripping member 218 allows the spring to return inner shaft end 216 to an initial position, as shown in FIG. 17.

Figure 21:
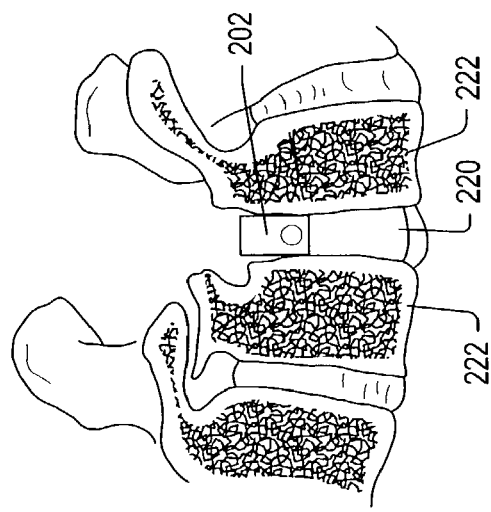
FIG. 21 depicts a representation of an embodiment of a modular tip inserted in a disc space after removal of a shaft from the modular tip.
Figure 20:
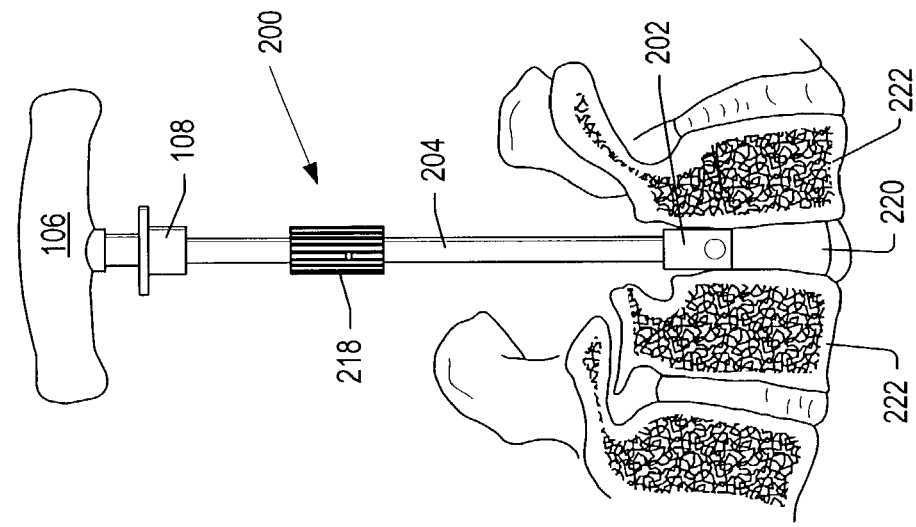
FIG. 20 depicts a representation of an embodiment of a modular tip distractor inserted in a disc space after distraction of vertebrae.
Figure 19:
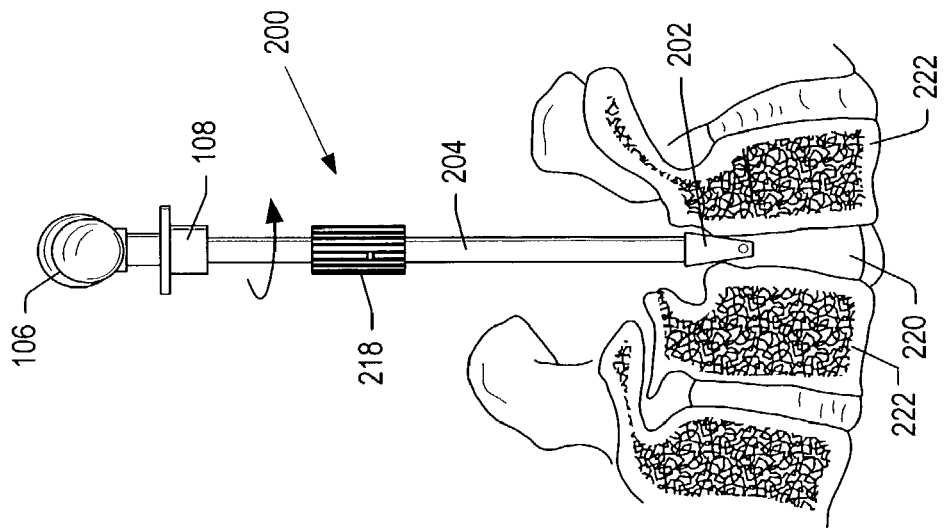
FIG. 19 depicts a representation of an embodiment of a modular tip distractor inserted in a disc space prior to distraction of vertebrae.

During a spinal fusion procedure, properly sized modular tip 202 may be coupled to shaft 204. Handle 106 may be attached to shaft 204 to form modular tip distractor 200, as shown in FIG. 15. A narrow portion of modular tip 202 may be inserted into a disc space. FIG. 19 shows a representation of modular tip distractor 200 positioned in disc space 220 prior to distraction of vertebrae 222. Handle 106 may be oriented substantially perpendicular to the spinal column. Handle 106 may be rotated to rotate modular tip 202 so that the modular tip establishes a desired separation distance between vertebrae. FIG. 20 shows a representation of modular tip distractor 200 positioned in disc space 220 after distraction of vertebrae 222 to a desired separation distance. After tip 202 establishes the desired separation distance between vertebrae 222, gripping member 218 may be rotated so that shaft 204 is removable from modular tip 202. FIG. 21 depicts a representation of modular tip 202 left within disc space 220. Leaving modular tip 202 in disc space 220 without a shaft may decrease a chance of inadvertently changing the position of vertebrae 222 by accidentally moving or contacting the shaft. Keeping the modular shaft out of the disc space allows disc preparation and insertion instruments to be placed more easily on the side opposite of the distraction. When desired, shaft 204 may be reinserted into modular tip 202. Handle 106 may be rotated to rotate modular tip 202 so that the modular tip may be easily removed from the patient.

In some embodiments, a shaft of a modular tip distractor may be coupled to the tip by threading. The threading may allow the tip to be rotated when the tip is positioned between vertebrae in a first direction (e.g., clockwise) to establish a desired separation distance between the vertebrae. The shaft may be rotated in a second direction (e.g., counterclockwise) to allow removal of the tip from the shaft. When desired, the shaft may be threaded to the tip again to allow for removal of the tip from between the vertebrae.

In some embodiments, a tip of a modular tip distractor may include a keyway. A shaft of the modular tip distractor may include a protrusion or protrusions that engage surfaces of the tip defining the keyway. Positioning the shaft in the keyway of the tip may couple the shaft to the modular tip so that the tip can be rotated between vertebrae to establish a desired separation distance between the vertebrae. The shaft may be removed from the keyway to leave the tip positioned between the vertebrae. When desired, the shaft may be reinserted into the tip to allow for removal of the tip from between the vertebrae.

Figure 22:
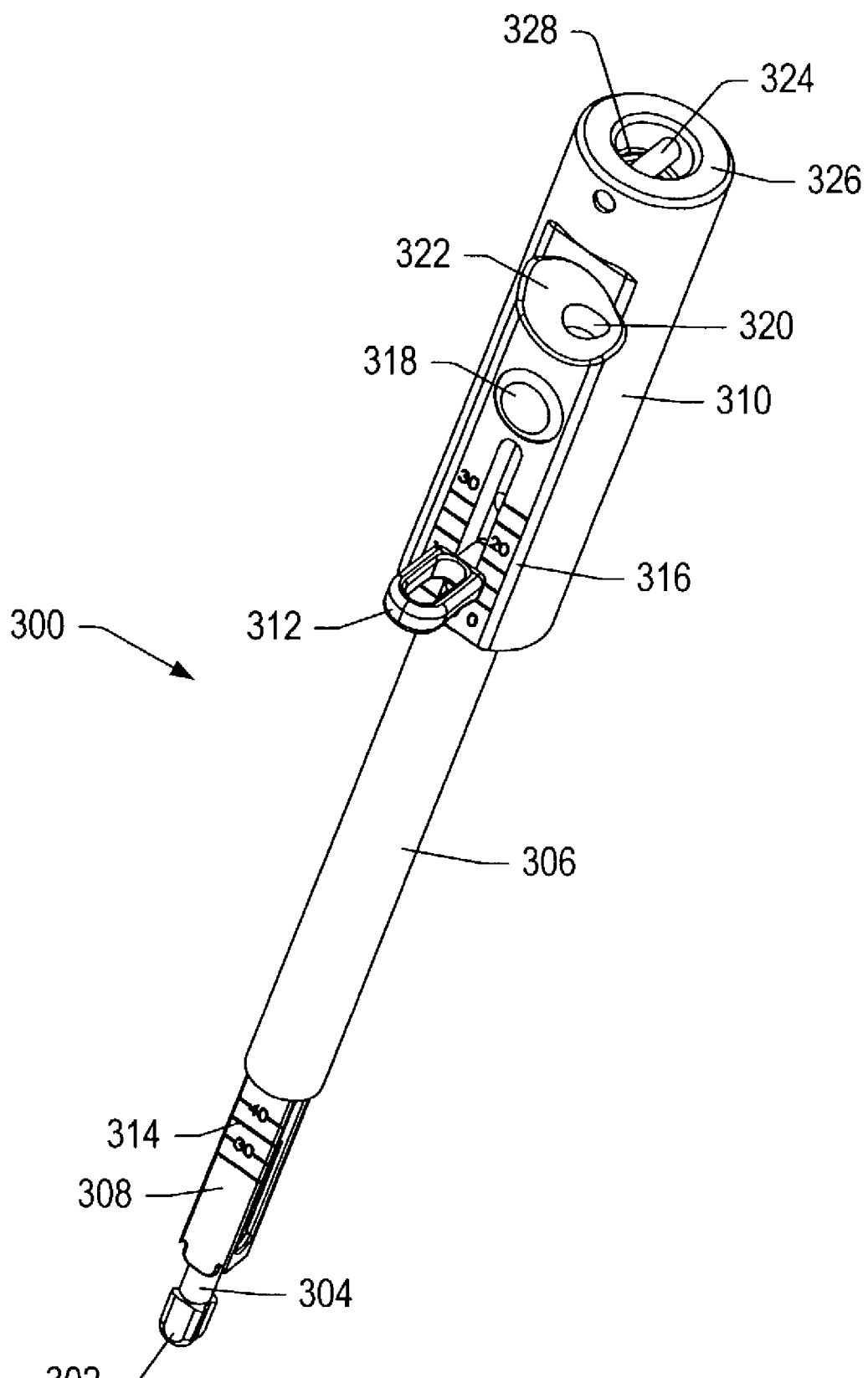
FIG. 22 depicts a perspective view of an embodiment of a chisel for preparing bone for implant insertion.
Figure 23:
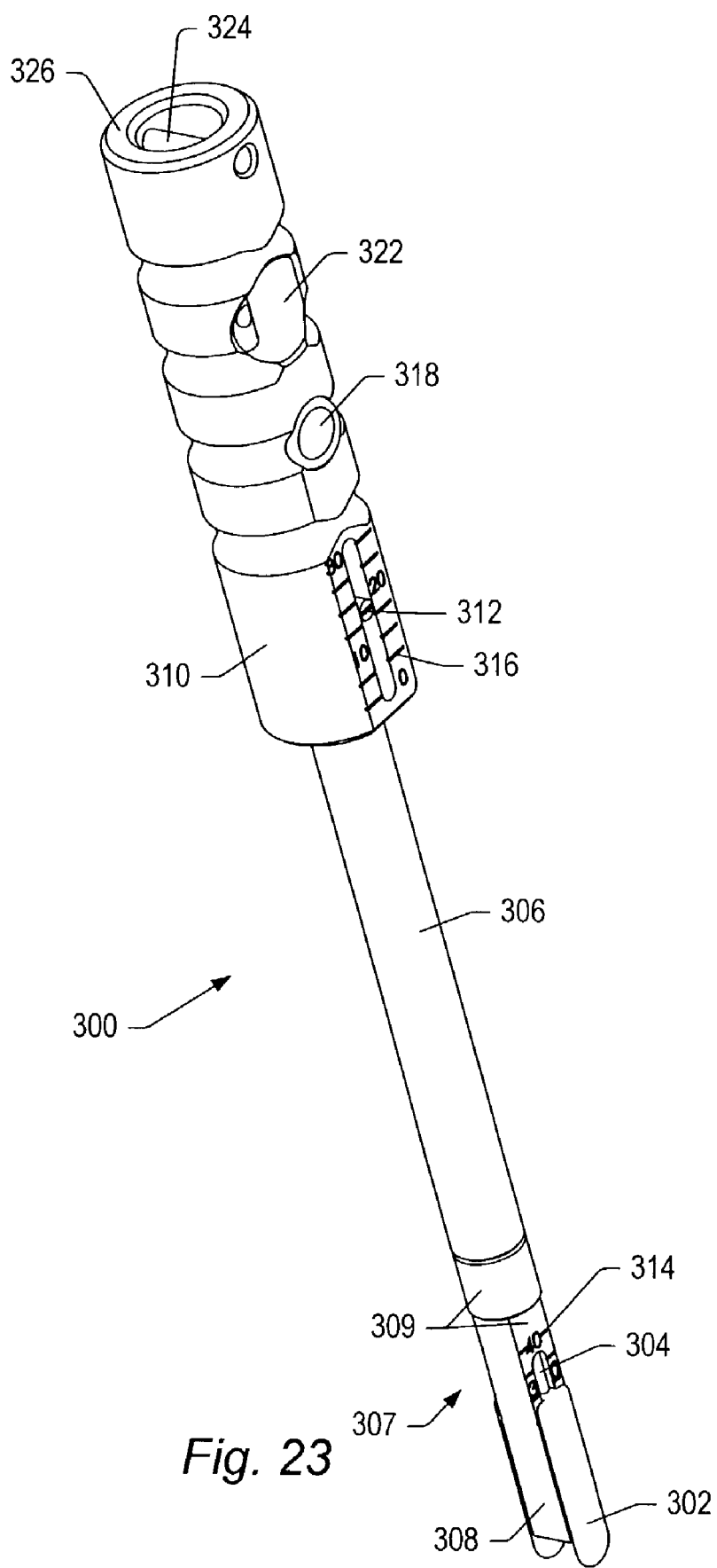
FIG. 23 depicts a perspective view of an embodiment of a chisel for preparing bone for implant insertion.

Disc preparation instruments may include chisel 300 for preparing a disc for an implant. FIGS. 22 and 23 depict perspective views of chisel embodiments. Chisel 300 may include guide 302, inner shaft 304, outer shaft 306, blade assembly 307, blades 308, blade base 309, and handle 310.

Guide 302 may establish a separation distance between vertebrae. An end of guide 302 may be rounded or tapered to facilitate insertion of portions of chisel 300 in a disc space. Guide 302 may be coupled to inner shaft 304. Inner shaft 304 may be telescopically positioned within outer shaft 306. Outer shaft 306 may be attached to blades 308 at a first end and to handle 310 at a second end. Indicator 312 may be coupled to inner shaft 304 in handle 310 of chisel 300. Indicator 312 may inhibit inner shaft 304 from being removed from outer shaft 306 and handle 310. Indicator 312 and proximal indicia 316 on handle 310 may be used to determine an insertion depth of blades 308 into a disc space.

As depicted in FIG. 22, indicator 312 may extend beyond a surface of handle 310. Extended indicator 312 may be used to easily move guide 302 relative to blades 308. The ability to move guide 302 relative to blades 308 may aid in cleaning chisel 300.

In some embodiments, guide 302 is removably attachable to inner shaft 304. Having removably attachable guide 302 may aid in cleaning chisel 300. In some embodiments, blade assembly 307 may include blades 308 coupled to blade base 309. Blade base 309 may be threaded onto outer shaft 306. In other embodiments, other types of fastening systems may be used to join the chisel blades to the outer shaft. Replaceable (modular) blades 308 or blade assemblies 307 may reduce manufacturing costs for a complete set of chisels and allow for easier cleaning.

Blades 308 may cut channels in bone for an implant. Blades 308 or blade base 309 may include distal indicia 314 that indicate depth of the chisel blades in a disc space. In some embodiments, distal indicia 314 on blades 308 include numerical indicia etched into surfaces of the blade. In some embodiments, blades 308 are colored a first color to a maximum safe insertion depth, and a second distinct color above the first color. For example, blades 308 may be colored gold from a distal end to the maximum safe insertion depth, and may be colored silver above the maximum depth. During use, if a user can see the first color, the user will know that the chisel is not inserted into the disc space beyond a safe depth. Chisel 300 may also have other types of depth indicators.

Handle 310 may include proximal indicia 316, release button 318, shaft passage 320, opening 322, rod 324, and strike surface 326. Proximal indicia 316 may be numerical markings on handle 310. The numerical markings relative to indicator 312 may indicate a depth of distal ends of blades 308 relative to a proximal end of guide 302 in a particular measurement unit. In an embodiment, the markings indicate millimeters of insertion. When guide 302 is inserted into a disc space, blades 308 may contact bone with indicator 312 at a nonzero marking. For example, indicator 312 may be at a marking of 3 when blades 308 contact vertebrae. The initial indicator marking may be noted, and a simple difference calculation may be used to determine the depth of insertion as the chisel blades are inserted into the disc space. For example, if the initial location of indicator 312 is adjacent to marking 3, and bone is cut away until the indicator is adjacent to marking 15, then blades 308 have been inserted into the disc space 12 units. In some embodiments, a range of motion of blades 308 relative to guide 302 is limited to about 30 mm. In other embodiments, smaller or larger ranges of motion may be allowed.

When release button 318 is pushed, blade assembly 307, blades 308, blade base 309, outer shaft 306, and handle 310 may be able to move relative to guide 302 and inner shaft 304. Inner shaft 304 may include an indention that mates with a detent of the handle. The detent may be positioned in the indention to fix the position of inner shaft 304 relative to handle 310 when guide 302 is extended away from blades 308. FIG. 22 shows an embodiment of chisel 300 when the position of inner shaft 304 is fixed relative to the position of handle 310. Guide 302 may be inserted into a disc space to establish a separation distance between vertebrae when the position of inner shaft 304 is fixed relative to the position of handle 310. Pushing button 318 releases blades 308 so that the blades may be used to simultaneously form channels in adjacent bone.

Shaft passage 320 in handle 310 provides room for movement of inner shaft 304. Shaft passage 320 is shown in FIG. 22 in opening 322. Opening 322 may be provided to reduce weight of chisel 300.

Rod 324 may be placed in a top portion of handle 310. Rod 324 may be placed in slots in walls of handle 310. Spring 328 may be positioned beneath rod 324. Rod 324 may be an engagement pin for a slap hammer or other instrument used to remove chisel 300 from a disc space. Spring 328 may limit downward application of force by the slap hammer or other instrument to chisel 300. Spring 328 may also help to hold the slap hammer or other instrument on chisel 300.

Handle 310 may include strike surface 326. A mallet or other force instrument may be impacted against strike surface 326 to drive blades 308 so that the blades remove bone material and/or cartilage and form channels in adjacent vertebral end plates.

FIGS. 22 and 23 show only one side of handle 310 and blades 308 of chisel 300. In some embodiments, proximal indicia 316 and distal indicia 314 may only be formed on one side of chisel 300. In other embodiments, proximal indicia 316 and distal indicia 314 may be formed on opposite sides of chisel 300, and indicators 312 may extend outwards from two sides of inner shaft 304.

Figure 24:
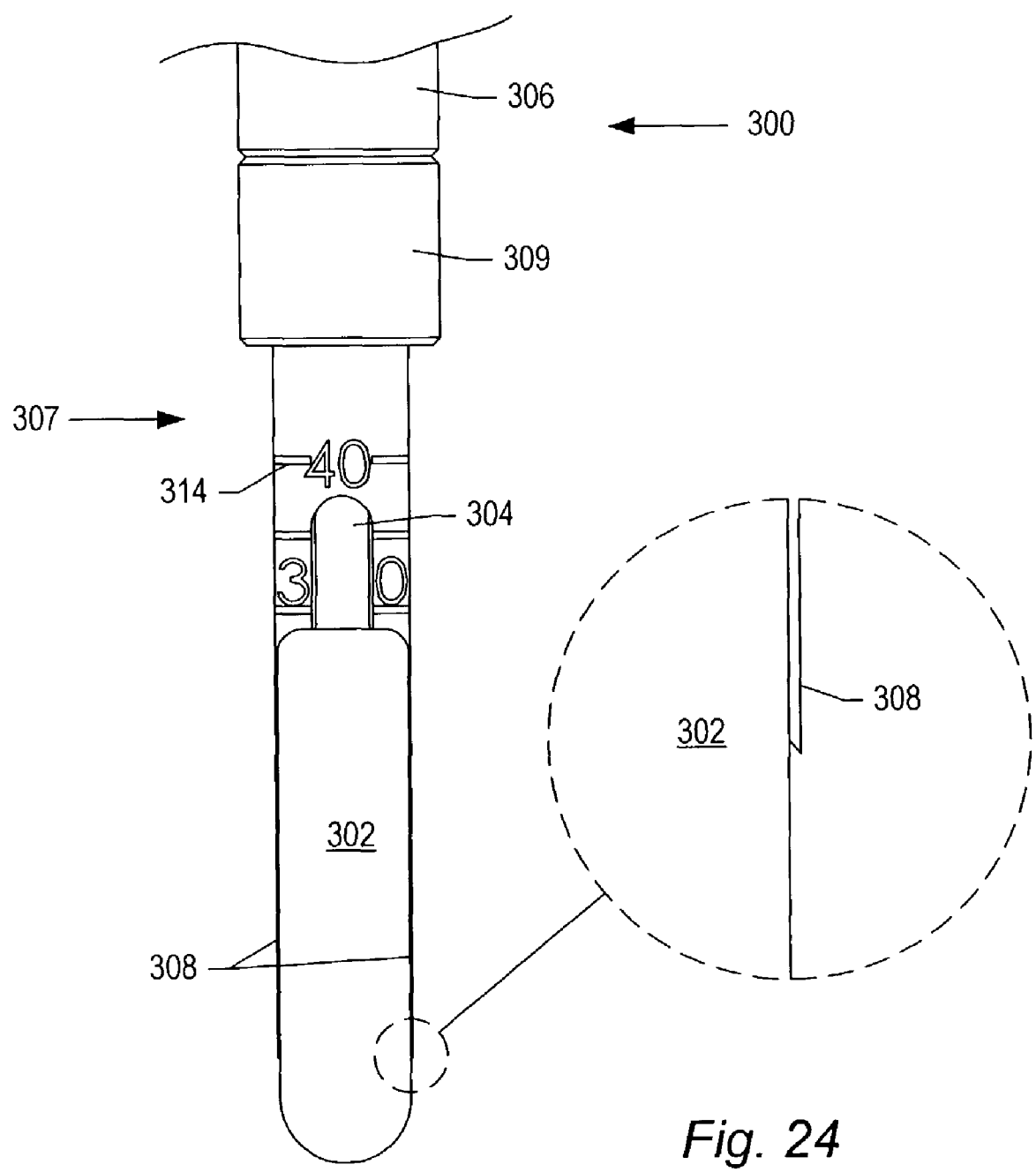
FIG. 24 depicts a front view of a portion of an embodiment of a chisel, including an inset view that shows a chisel blade relative to a chisel guide.

FIG. 24 shows a detailed view of a portion of an embodiment of chisel 300. As shown in the inset view, blade 308 extends beyond an outer surface of guide 302. Blades that are able to cut various channel depths in adjacent bones may be provided in an instrumentation set. The depth of cut into a bone may be from about 0.001 mm to about 5 mm.

To use chisel 300, proper guides 302 and blades 308 or blade assembly 307 are coupled to outer shaft 306. Inner shaft 304 is positioned within chisel 300 so that the inner shaft is inhibited from moving relative to handle 310. Guide 302 is then placed in a disc space and impacted to a desired depth. Button 318 is pushed to release handle 310 and blades 308 relative to guide 302. The initial position of indicator 312 relative to proximal indicia 316 may be noted when the blades 308 first contact vertebrae. Handle 310 may be impacted to drive blades 308 into the vertebrae. Depth of the blades 308 in the vertebrae may be determined by subtracting a position of indicator 312 at a cutting depth from the initial position of the indicator. When a desired depth is obtained, a slap hammer may be attached to rod 324. The slap hammer may be used to remove chisel 300 from the disc space.

Figure 25:
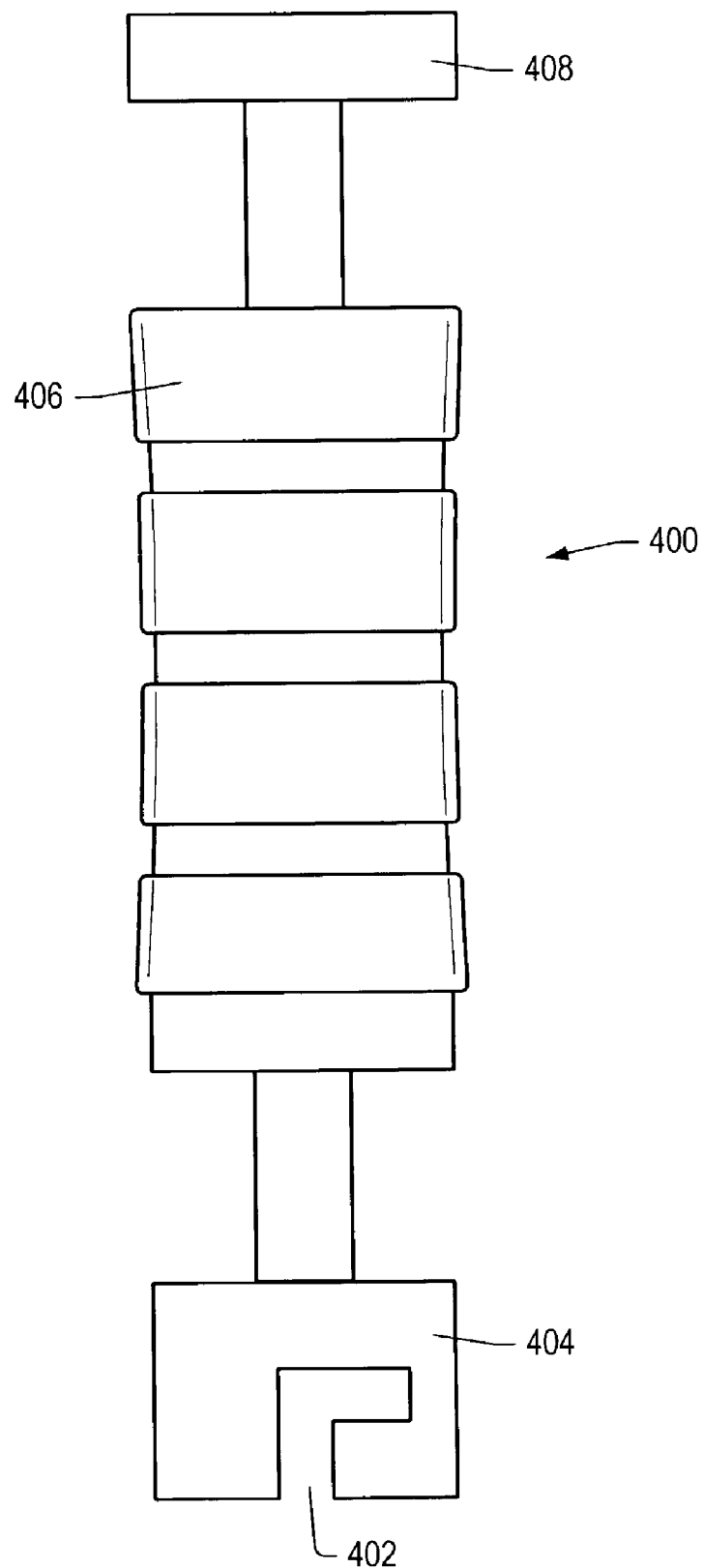
FIG. 25 depicts an embodiment of a slap hammer.

FIG. 25 shows an embodiment of slap hammer 400 that may be used with a chisel or other instrument. Slot 402 of end 404 may engage a rod in a handle of the chisel. A spring in the handle of the chisel may be compressed when the end is inserted into the handle. Slap hammer 400 may be rotated to engage the rod in the horizontal portion of slot 402. Slide 406 of slap hammer 400 may be grasped and repeatedly moved against stop 408 to provide an impulse force to remove the chisel from the disc space. After removing the chisel from the disc space, slap hammer 400 may be removed from the chisel.

An implant inserter may be used to place an implant in a disc space. In some embodiments, the implant inserter may grasp side surfaces of an implant. Many implant inserters include an end that engages an opening in an end surface of an implant. Forming an opening in an end of an implant may weaken the compressive load handling ability of the implant. In some implant embodiments formed of bone, forming an opening in the bone implant and/or attaching the implant to the inserter may result in breakage or fracturing of the implant. The ability to grasp a side surface of an implant may allow the implant to have a solid end. Having a solid end may strengthen the implant and inhibit the need to apply forces to the implant that may break or fracture the implant. Also, the use of an implant inserter that grasps side surfaces of the implant may avoid application of rotational forces to the implant when the implant inserter is removed from the implant.

Figure 26:
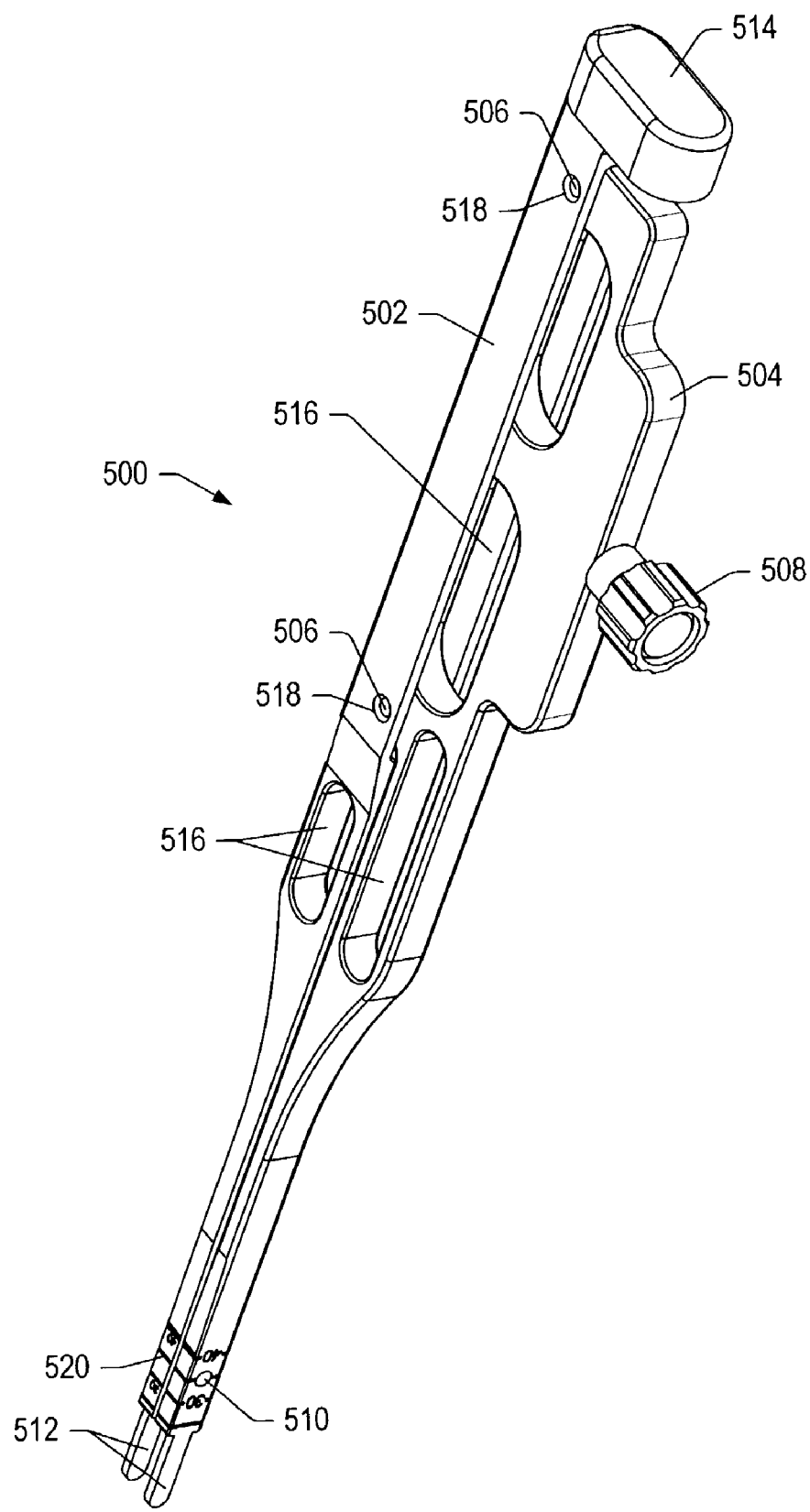
FIG. 26 depicts an embodiment of an implant inserter.

FIG. 26 depicts an embodiment of implant inserter 500 that places an implant in a prepared disc space. Inserter 500 may include first member 502, second member 504, linking pins 506, locking member 508, pin 510, arms 512, and strike surface 514. First member 502 and second member 504 may include openings 516. Openings 516 may reduce the weight of inserter 500. Linking pins 506 positioned in holes 518 in first member 502 and slots of second member 504 allow for lateral adjustment of position of the second member relative to the first member. A threaded shaft may be coupled to first member 502 and extend through second member 504. Locking member 508 may be threaded to the threaded shaft. Locking member 508 may be affixed to the threaded shaft to inhibit inserter 500 from being disassembled after assembly. Springs that bias first member 502 away from second member 504 may be placed between the first member and the second member before locking member 508 is attached to the threaded shaft.

Clockwise rotation of locking member 508 may force second member 504 towards first member 502. Arms 512 of inserter 500 may grasp grooves of an implant positioned between the arms (e.g., side grooves 46 of implant 40 depicted in FIG. 1). Arms 512 may be roughened, grooved, knurled, shot peened, or otherwise textured to promote good contact between the implant and arms 512. Counterclockwise rotation of locking member 508 may allow springs between first member 502 and second member 504 to force the first member away from the second member and widen a distance between arms 512 so that an implant positioned between the arms may be released from the arms. In other embodiments, threading of the threaded shaft and locking member may be reversed so that clockwise rotation of the compression member allows the first member to move away from the second member.

Pin 510 may be secured to one arm and slidably positioned in an opening of the other arm. Pin 510 may inhibit arms 512 from separating during implant insertion if implant inserter 500 is twisted during insertion of the implant. Pin 510 may be made of a material that resists galling.

Implant inserter 500 may include strike surface 514. A mallet or other impact tool may hit strike surface 514 during insertion of an implant. Strike surface 514 may be located substantially directly over an implant positioned between arms 512 to apply a force distributed evenly across the implant surface.

Indicia 520 may be placed on inserter arms 512. Indicia 520 may be used to estimate an insertion depth of an implant in a disc space.

Figure 27:
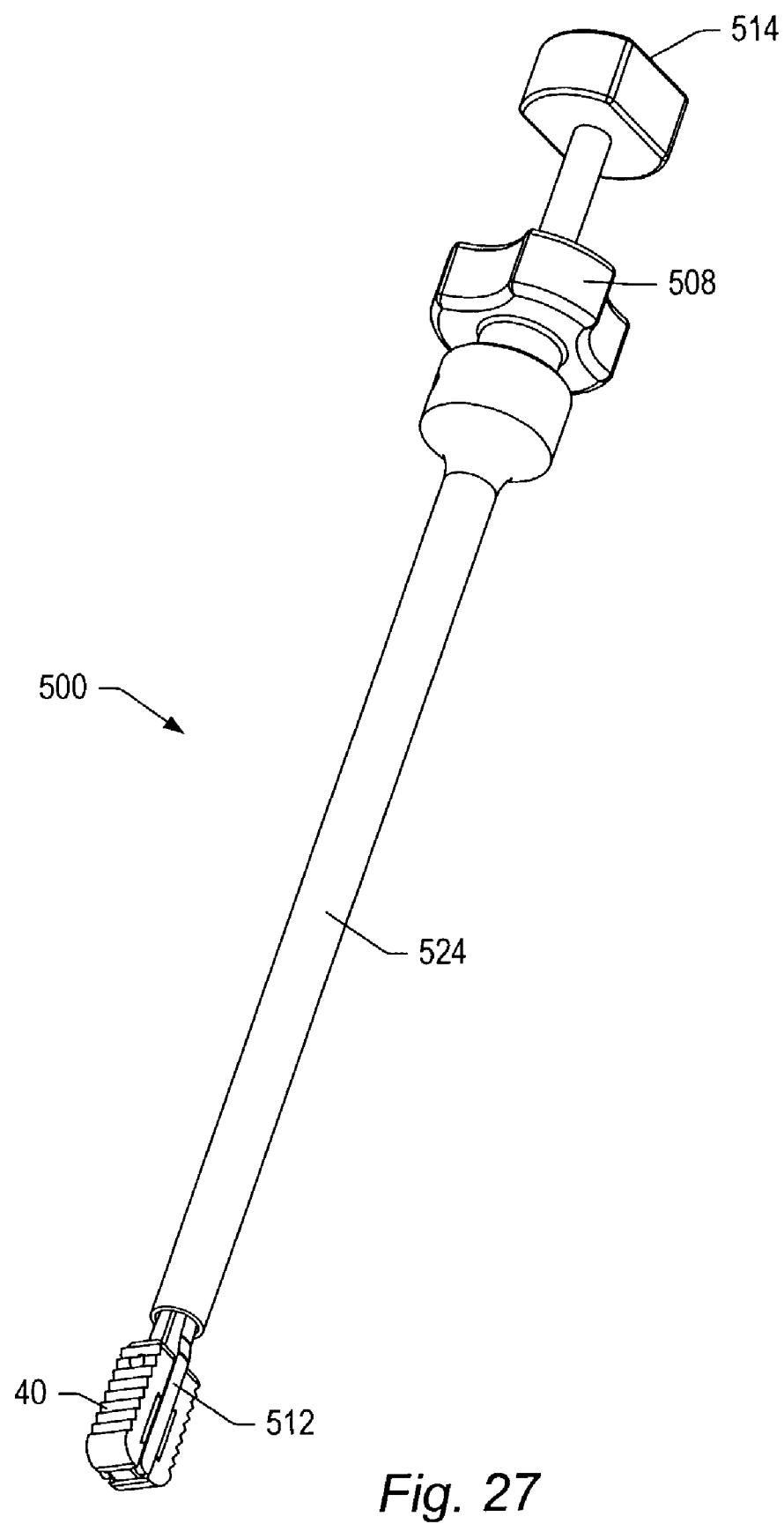
FIG. 27 depicts an embodiment of an implant inserter.

FIG. 27 shows another embodiment of implant inserter 500. Implant inserter 500 may advantageously have a low profile. A low profile allows a surgeon to see an insertion site during a bone fusion procedure. Implant inserter 500 may include outer shaft 524. Upper portions of arms 512 of implant inserter 500 may be tapered so that portions of the arms that grasp an implant are wider than other portions of the arms. When locking member 508 is rotated clockwise, the locking member drives outer shaft 524 towards implant 40 positioned between arms 512. An end of outer shaft 524 contacts wide sections of arms 512 so that a force is applied to the arms to securely hold the implant. Rotation of locking member 508 in an opposite direction releases outer shaft 524 and allows arms 512 to spread back to a separated position to release the implant.

An implant may be installed using a minimally invasive procedure. A minimally invasive procedure may result in faster recovery and/or minimal scarring of the patient. In some embodiments, a port may be inserted into a patient to provide access to vertebrae that are to be fused together. Instruments (e.g., distractors, chisels, and implant inserters) may be inserted into the port during an implant insertion procedure.

To fuse two vertebra together using implants, the implants may be formed of members that are joined together to form the implant. Portions of bone and/or other material may be used as material for the members. The members may include rotational joints that allow the members to be joined together and inhibit axial movement of the members relative to each other. The members may be pinned together or otherwise joined together to inhibit rotation of the members relative to each other. The resulting implant may be provided with a desired lordotic alignment and/or texturing that inhibits backout of an implant from a disc space. If the implant is formed of bone, the implant members may be processed in a freeze-dried state. Before insertion into a patient, the implant may be reconstituted by soaking the implant in an aqueous solution.

After, or simultaneously with, reconstitution of the implant, a disc space for the implant may be formed in a patient. In a posterior procedure, an incision may be made and portions of a spinous process may be removed to provide access to the disc. The spinal cord or cauda equina may be retracted.

A discectomy may be performed to remove disc material from a first side of a disc and form a first disc space. A distractor may be positioned in the first disc space to establish a separation distance between the vertebrae. In an embodiment, the distractor is a modular tip distractor, and the distractor tip is left in the first disc space while the shaft of the distractor is removed. A discectomy may be performed on a second side of the disc to form a second disc space. A chisel may be used to remove portions of vertebral bone and form channels in the vertebral end plates adjacent to the second disc space. Removing bone portions may promote bone growth that couples an implant inserted in the disc space to the vertebrae. Osteophytes may be removed to make insertion of the implant easier. A first implant may be attached to an implant inserter. The first implant may be impacted into the prepared disc space on the second side of the disc. The first implant may be an implant with a blunt anterior end, such as an implant depicted in FIGS. 8-11. The first implant may be released from the inserter. The distractor may be removed from the first side of the disc. Vertebral bone adjacent to the first disc space may be removed using a chisel to form channels in vertebral bone. Packing material may be packed in a space around the first implant. In an embodiment, packing material may be cancellous bone, synthetic bone, or other bone graft material. A second implant may be inserted on the first side of the disc using an implant inserter. The second implant may be an implant with a tapered anterior end, such as an implant depicted in FIGS. 1, 2, 5, and 6. Insertion of the second implant may force the packing material between the second implant and the first implant and/or between the second implant and remaining disc.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method of inserting an implant in a disc space, comprising:
   gripping the implant with a first and second arms of an insertion instrument, wherein the first and second arms of the insertion instrument are configured to hold the implant and wherein the insertion instrument further comprises:
      a locking member configured to move the first arm towards the second arm relative to a body of the insertion instrument, wherein the second arm remains stationary relative to the body of the insertion instrument; and
      an impact surface configured to receive an impact to drive the implant between vertebrae;
   positioning the implant above a disc space between the vertebrae using the insertion instrument;
   inserting the implant between the vertebrae; and
   releasing the implant from the insertion.

2. The method of claim 1, wherein a width of the first arm and a width of the second arm are sized to reside in grooves formed in sides of the implant.

3. The method of claim 2, wherein gripping the implant further comprises grasping the grooves of the implant by the first and second arms of the insertion instrument.

4. The method of claim 1, wherein a portion of the first arm and a portion of the second arm are configured to contact a posterior surface of the implant.

5. The method of claim 1, wherein the insertion instrument further comprises indicia configured to indicate an insertion depth of the implant into the disc space when the implant is coupled to the first arm and the second arm.

6. The method of claim 1, wherein inserting the implant between the vertebrae comprising impacting the insertion instrument via the impact surface thereof to drive the implant between the vertebrae.

7. The method of claim 1, wherein gripping the implant comprises rotating the locking member to move the first arm towards the second arm when the first arm and the second arm are positioned on opposite sides of the implant.

8. The method of claim 1, wherein the impact surface is coupled to the second arm.

9. The method of claim 1, wherein releasing the implant from the insertion instrument further comprises rotating the locking member to move the first arm away from the second arm.

10. A method of inserting an implant in an intervertebral disc space, comprising:
   rotating a locking member of an insertion instrument in a first direction to move a first arm of the insertion instrument towards a second arm of the insertion instrument relative to a body of the insertion instrument, wherein the second arm of the insertion instrument remains stationary relative to the body of the insertion instrument;
   grasping the implant with the first and second arms of the insertion instrument;
   inserting the implant in the intervertebral disc space; and
   releasing the implant from the insertion instrument by rotating the locking member of the insertion instrument in a second direction to move the first arm of the insertion instrument away from the second arm of the insertion instrument, wherein the second arm of the insertion instrument remains stationary relative to the body of the insertion instrument.

11. The method of claim 10, wherein inserting the implant further comprises striking an impact surface of the insertion instrument to drive the implant to an insertion depth in the intervertebral disc space.

12. The method of claim 10, wherein rotating the locking member of the insertion instrument in the second direction allows springs between the first and second arms to force the first arm of the insertion instrument away from the second arm of the insertion instrument and widen a distance between the first and second arms.

13. The method of claim 10, wherein a pin is secured to the first arm and slidably positioned in an opening of the second arm.

14. The method of claim 10, wherein a pin is secured to the second arm and slidably positioned in an opening of the first arm.

* * * * *